US010036047B2

(12) United States Patent
Yan et al.

(10) Patent No.: US 10,036,047 B2
(45) Date of Patent: Jul. 31, 2018

(54) METHODS FOR HYDROXYLATING PHENYLPROPANOIDS

(71) Applicant: University of Georgia Research Foundation, Inc., Athens, GA (US)

(72) Inventors: Yajun Yan, Athens, GA (US); Yuheng Lin, Marietta, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 14/300,440

(22) Filed: Jun. 10, 2014

(65) Prior Publication Data

US 2014/0363858 A1 Dec. 11, 2014

Related U.S. Application Data

(60) Provisional application No. 61/833,173, filed on Jun. 10, 2013.

(51) Int. Cl.
| | |
|---|---|
| *C12P 7/06* | (2006.01) |
| *C12P 7/42* | (2006.01) |
| *C12N 9/02* | (2006.01) |
| *C12N 9/88* | (2006.01) |
| *C12N 9/90* | (2006.01) |
| *C12P 17/06* | (2006.01) |
| *C12P 7/22* | (2006.01) |
| *C12N 9/06* | (2006.01) |

(52) U.S. Cl.
CPC ............ *C12P 17/06* (2013.01); *C12N 9/0028* (2013.01); *C12N 9/0071* (2013.01); *C12P 7/22* (2013.01); *C12Y 105/01036* (2013.01); *C12Y 114/14009* (2013.01)

(58) Field of Classification Search
CPC .................... C12N 9/0073; C12N 9/88; C12Y 114/14009; C12P 17/06; C12P 7/22
USPC ....... 435/146, 156, 252.33, 252.3, 189, 195, 435/158
See application file for complete search history.

(56) References Cited

U.S. PATENT DOCUMENTS

| | | | |
|---|---|---|---|
| 4,703,004 | A | 10/1987 | Hopp et al. |
| 4,782,137 | A | 11/1988 | Hopp et al. |
| 5,594,115 | A | 1/1997 | Sharma |
| 5,935,824 | A | 8/1999 | Sgarlato |
| 8,809,028 | B2 | 8/2014 | Yan et al. |
| 2013/0130340 | A1 | 5/2013 | Yan et al. |

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*
Furuya et al. Appld Microbiol. Biotecol 2013, 98(3), abstract).*
National Center for Biotechnology Information, National Library of Medicine, National Institutes of Health, GenBank Locus CAA82321, Accession No. CAA82321, "4-hydroxyphenylacetic hydroxylase [*Escherichia coli*]," [online]. Bethesda, MD [retrieved on Oct. 3, 2015]. Retrieved from the Internet: ncbi.nlm.nih.gov/protein/CAA82321.1; 2 pgs.
National Center for Biotechnology Information, National Library of Medicine, National Institutes of Health, GenBank Locus CAA82322, Accession No. CAA82322, "flavin:NADH oxidoreductase component of the 4-HPA 3-monooxygenase [*Escherichia coli*]," [online]. Bethesda, MD [retrieved on Oct. 3, 2015]. Retrieved from the Internet: ncbi.nlm.nih.gov/protein/CAA82322.2; 2 pgs.
Spectral Database for Organic Compounds, SDBS No. 23227, accessed online on Oct. 3, 2015 at sdbs.db.aist.go.jp/sdbs/cgibin/direct_frame_disp.cgi?sdbsno=23227.
Amor et al., "Biotransformation of naringenin to eriodictyol by *Saccharomyces cerevisiea* functionally expressing flavonoid 3' hydroxylase" Nat Prod Commun, 2010; 5(12), 1893-8.
Brisdelli et al., "Resveratrol: a natural polyphenol with multiple chemopreventive properties" Curr Drug Metab, Jul. 2009; 10(6), 530-46.
Choi et al., "Engineering of daidzein 3'-hydroxylase P450 enzyme into catalytically self-sufficient cytochrome P450" Microb Cell Fact, 2012; 11, 81.
Encarnacion et al., "Isolation of eriodictyol identical with huazhongilexone from Solanum hindsianum" Acta Chem Scand, 1999; 53(5):375-7.
Gerhardt et al. (eds.) *Methods for General and Molecular Bacteriology*, American Society for Microbiology, 1994; Cover page, publisher's page, and chapters 13-14 and 16-18.
Han et al., "A New Synthesis of Stilbene Natural Product Piceatannol" Bulletin of the Korean Chemical Society 2008; 29(9):1800-2.
Kille et al., "Regio- and stereoselectivity of P450-catalysed hydroxylation of steroids controlled by laboratory evolution" Nat Chem, 2011; 3(9):738-43.
Kim et al., "Crystal structure of the oxygenase component (HpaB) of the 4-hydroxyphenylacetate 3-monooxygenase from Thermus thermophilus HB8" J Biol. Chem, 2007; 282(45), 33107-17.
Kim et al., "Generation of the human metabolite piceatannol from the anticancer-preventive agent resveratrol by bacterial cytochrome P450 BM3." Drug Metab Dispos, 2009; 37(5), 932-6.
Lee et al., "Regioselective hydroxylation of trans-resveratrol via inhibition of tyrosinase from Streptomyces avermitilis MA4680" ACS Chem Biol, 2012; 7(10), 1687-92.
Li et al., "Isolation, characterization and crystal structure of natural eremophilenolide from *Ligularia sagitta*" Zeitschrift Fur Naturforschung Section B—a Journal of Chemical Sciences, 2004; 59(b):921-4.

(Continued)

*Primary Examiner* — Tekchand Saidha
*Assistant Examiner* — Mohammad Y Meah
(74) *Attorney, Agent, or Firm* — Mueting, Raasch & Gebhardt, P.A.

(57) ABSTRACT

Provided herein are methods for producing an ortho-hydroxylated phenylpropanoid. In one embodiment the method includes culturing a microbe that includes HpaBC activity in the presence of a phenylpropanoid substrate. Also provided are genetically engineered microbes engineered to have greater levels of HpaB and/or HpaC than a control microbe.

21 Claims, 13 Drawing Sheets

(56) References Cited

OTHER PUBLICATIONS

Lin et al., "Biosynthesis of caffeic acid in *Escherichia coli* using its endogenous hydroxylase complex" Microb Cell Fact, 2012; 11(1):42.

Lin et al., "Biotechnological production of plant-specific hydroxylated phenylpropanoids" Biotechnol Bioeng, 2014; 111(9):1895-9.

Lin et al., "Biotechnological production of plant-specific hydroxylated phenylpropanoids" Supplementary Information, 2014; 13 pages.

Louie et al., "Coordinated production and utilization of FADH2 by NAD(P)H-flavin oxidoreductase and 4-hydroxyphenylacetate 3-monooxygenase" Biochemistry (Mosc) 2003; 42(24):7509-17.

Masamoto et al., "Inhibitory effects of esculetin on melanin biosynthesis" Biol Pharm Bull, 2004; 27(3):422-5.

Pandey et al., "Screening of bacterial cytochrome P450s responsible for regiospecific hydroxylation of (iso)flavonoids" Enzyme Microb Technol, 2011; 48(4-5):386-92.

Piotrowska et al., "Biological activity of piceatannol: leaving the shadow of resveratrol" Mutat Res, 2012; 750(1):60-82.

Potter et al., "The cancer preventative agent resveratrol is converted to the anticancer agent piceatannol by the cytochrome P450 enzyme CYP1B1" Br J Cancer, 2002; 86:774-8.

Prieto et al., "Characterization of an *Escherichia coli* aromatic hydroxylase with a broad substrate range" J Bacteriol, 1993; 175:2162-7.

Prieto et al., "Molecular characterization of 4-hydroxyphenylacetate 3-hydroxylase of *Escherichia coli*. A two-protein component enzyme" J. Biol Chem, 1994; 269:22823-9.

Sambrook et al., *Molecular Cloning: A Laboratory Manual*, Cold Spring Harbor Laboratory Press: New York; 1989. Cover page, title page and table of contents.

Tatusova et al., "BLAST 2 Sequences, a new tool for comparing protein and nucleotide sequences" FEMS Microbiol Lett, 1999; 174, 247-50.

Ullrich et al., "Enzymatic hydroxylation of aromatic compounds" Cell Mol Life Sci, 2007; 64(3):271-93.

Urlacher et al., "Cytochrome P450 monooxygenases: perspectives for synthetic application" Trends Biotechnol, 2006; 24(7):324-30.

Urlacher et al., "Cytochrome P450 monooxygenases: an update on perspectives for synthetic application" Trends Biotechnol, 2012; 30:26-36.

Xun et al., "Characterization of 4-hydroxyphenylacetate 3-hydroxylase (HpaB) of *Escherichia coli* as a reduced flavin adenine dinucleotide-utilizing monooxygenase" Appl. Environ. Microbiol, 2000; 66:481-6.

Yang et al., "Esculetin induces apoptosis and inhibits adipogenesis in 3T3-L1 cells" Obesity (Silver Spring), 2006; 14(10):1691-9.

Kim et al., "Crystal structure of the flavin reductase component (HpaC) of 4-hydroxyphenylacetate 3-monooxygenase from *Thermus thermophiles* HB8: Structural basis for the flavin affinity" Proteins, Feb. 15, 2008; 70(3):718-30. Available online Aug. 29, 2007.

* cited by examiner

Figure 1

| Native substrate | 4HPA |
| --- | --- |
| Verified substrates | Phenol, p-Cresol, L-Tyrosine, p-Coumaric acid |
| Substrates to test | Umbellifrone, Resveratrol, Naringenin |

Figure 13

SEQ ID NO:1

MKPEDFRASTQRPFTGEEYLKSLQDGREIYIYGERVKDVTTHPAFRNAAASVAQLYDALHKPEMQDSLCW
NTDTGSGGYTHKFFRVAKSADDLRHERDAIAEWSRLSYGWMGRTPDYKAAFGCALGGTPGFYGQFEQNAR
NWYTRIQETGLYFNHAIVNPPIDRHLPTDKVKDVYIKLEKETDAGIIVSGAKVVATNSALTHYNMIGFGS
AQVMGENPDFALMFVAPMDADGVKLISRASYEMVAGATGSPYDYPLSSRFDENDAILVMDNVLIPWENVL
LYRDFDRCRRWTMEGGFARMYPLQACVRLAVKLDFITALLKKSLECTGTLEFRGVQADLGEVVAWRNTFW
ALSDSMCSEATPWVNGAYLPDRAALQTYRVLAPMAYAKIKNIIERNVTSGLIYLPSSARDLNNPQIDQYL
AKYVRGSNGMDHVQRIKILKLMWDAIGSEFGGRHELYEINYSGSQDEIRLQCLRQAQSSGNMDKMMAMVD
RCLSEYDQNGWTVPHLNNDDINMLDKLLK

SEQ ID NO:2

MQLDEQRLRFRDAMASLSAAVNIITTEGDAGQCGITATAVCSVTDTPPSLMVCINANSAMNFVFQGNGKL
CVNVLNHEQELMARHFAGMTGMAMEERFSLSCWQKGPLAQPVLKGSLASLEGEIRDVQAIGTHLVYLVEI
KNIILSAEGHGLIYFKKRFHPVMLEMEAAI

METHODS FOR HYDROXYLATING PHENYLPROPANOIDS

CROSS-REFERENCE TO RELATED APPLICATIONS

This application claims the benefit of U.S. Provisional Application Ser. No. 61/833,173, filed Jun. 10, 2013, which is incorporated by reference herein.

SEQUENCE LISTING

This application contains a Sequence Listing electronically submitted via EFS-Web to the U. S. Patent and Trademark Office as an ASCII text file entitled "US14300440_ST25.txt" having a size of 7 kilobytes and created on Jul. 28, 2014. The information contained in the Sequence Listing is incorporated by reference herein.

BACKGROUND

Phenylpropanoids including stilbenes, coumarins, and flavonoids are a major class of plant secondary metabolites that exhibit diverse molecule structures and broad pharmacological effects. Introduction of hydroxyl groups is a commonly-used strategy by nature to increase solubility, stability, structure diversity and biological activities of secondary metabolites. Recently, a variety of hydroxylated phenylpropanoid compounds were found to possess more attractive properties for potential pharmaceutical uses. For instance, piceatannol is a 3'-hydroxylated derivative of resveratrol, a well-known natural product for its anti-aging, anti-inflammatory, and cancer preventative effects (Brisdelli et al., *Curr. Drug Metab.*, 2009, 10, 530-546). Indeed, resveratrol, as a pro-drug, is eventually converted to piceatannol in human liver by cytochrome P450 (CYP) hydroxylase (Potter et al., *Br. J. Cancer*, 2002, 86, 774-778), while the latter has demonstrated additional functions, e.g. tyrosine kinase inhibition, cancer cell suppression, and antiparasitic activity (Piotrowska et al., *Mutat. Res.*, 2012, 750, 60-82). As another example, esculetin, a hydroxylated analogue of umbelliferone, has been shown to inhibit adipogenesis and induce apoptosis of maturing preadipocytes (Yang et al., *Obesity (Silver Spring)*, 2006, 14, 1691-1699). It also inhibits tyrosinase activity and the formation of melanin (Masamoto et al., *Biol. Pharm. Bull.*, 2004, 27, 422-425). Despite of their various functions, these hydroxylated metabolites usually exist at low abundance in nature, which hampers the exploration and application of their pharmacological properties.

Regioselective hydroxylation via synthetic chemistry approaches has been used to activate, derivatize, and functionalize inert carbons in complex compounds. However, these approaches are usually quite challenging, necessitating laborious protectiong and deprotection steps (Ullrich and Hofrichter, *Cell. Mol. Life. Sci.*, 2007, 64, 271-293). Alternatively, biocatalytic hydroxylation provides a facile and environmental friendly way for specific oxygen transfer. In past decades, cytochrome P450 hydroxylases remained to be the dominant group of enzymes that can be engineered for this purpose (Amor eta al., *Nat. Prod. Commun.*, 2010, 5, 1893-1898; Kille et al., *Nat. Chem.*, 80 2011, 3, 738-743, Urlacher and Girhard, *Trends Biotechnol.*, 2012, 30, 26-36, Urlacher and Eiben, *Trends Biotechnol.*, 2006, 24, 324-330). However, low coupling efficiency and low activity are among the most frequently encountered problems due to the catalytic mechanism of these enzymes (Urlacher and Girhard, *Trends Biotechnol.*, 2012, 30, 26-36; Urlacher and Eiben, *Trends Biotechnol.*, 2006, 24, 324-330). Recently, several microbial P450 hydroxylases were identified to catalyze the orthohydroxylation of stilbenes and flavonoids (Kim et al., *Drug Metab. Dispos.*, 2009, 37, 932-936; Lee et al., *ACS Chem. Biol.*, 2012, 7, 1687-1692; Choi et al., *Microb Cell Fact*, 2012, 11, 81; Pandey et al., *Enzyme Microb. Technol.*, 2011, 48, 386-392), however, the productivity (rate, yield and/or titer) was still low for scale-up application.

SUMMARY OF THE APPLICATION

Regio-selective hydroxylation of aromatic compounds such as phenylpropanoids is an important approach to activate, functionalize and derivatize these molecules for broader pharmaceutical applications. Provided herein is a novel approach for regioselective hydroxylation of aromatic compounds by a bacterial non-P450 monooxygenase. It is energy-saving and environmentally-friendly compared to current chemical hydroxylation approaches, and more efficient than current biological approaches using P450 enzymes. We have demonstrated its high conversion efficiency on some phenylpropanoids.

Provided herein are methods for producing an ortho-hydroxylated phenylpropanoid. In one embodiment the method includes culturing a microbe that includes HpaBC activity in the presence of a phenylpropanoid substrate. The culturing is under conditions suitable to ortho-hydroxylate the phenylpropanoid substrate to result in an ortho-hydroxylated phenylpropanoid. Optionally, the ortho-hydroxylated phenylpropanoid is isolated from the microbe, from the culture medium, or the combination thereof. In one embodiment, the culturing further includes adding the phenylpropanoid substrate. In one embodiment, the phenylpropanoid substrate is produced by the microbe.

In one embodiment, the phenylpropanoid substrate includes a first six-carbon ring and an additional cyclic structure, where the phenylpropanoid substrate has a structure of the formula

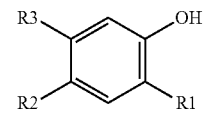

wherein R1 is the position the phenylpropanoid substrate is ortho-hydroxylated, wherein R2 is a divalent organic linking group that includes the additional cyclic structure or is joined to R3 to form the additional cyclic structure, and wherein R3 is a hydrogen or a nonring substituent. In one embodiment, the divalent organic linking group is a linear hydrocarbon group. In one embodiment, the linear hydrocarbon group includes between 0 and 20 carbons, and in one embodiment, the linear hydrocarbon group includes at least one unsaturated bond. In one embodiment, the additional cyclic structure is a 5 atom ring or a 6 atom ring. In one embodiment, the ring is a heterocycle.

In one embodiment, the R3 is selected from a halogen, a nitrile, a hydroxy, an alkoxy (OR), a nitrate, a nitrite, a sulfate (O—$SO_3R$), an amino ($NR_2$), a nitro, a sulfonate ($SO_2OR$), or a C1-C10 organic group, with each R independently being hydrogen or an organic group. In one embodiment, one or more hydrogen-bearing carbon atoms in the first six-carbon ring is substituted, wherein each substituent is selected from a halogen, a nitrile, a hydroxy, an alkoxy (OR), a nitrate, a nitrite, a sulfate (O—$SO_3R$), an amino ($NR_2$), a nitro, a sulfonate ($SO_2OR$), or a C1-C10 organic group, wherein each R is independently a hydrogen or an organic group. In one embodiment, one or more hydrogen-bearing carbon atoms in the additional cyclic structure is substituted, wherein each substituent is selected from a halogen, a nitrile, a hydroxy, an alkoxy (OR), a nitrate, a nitrite, a sulfate (O—$SO_3R$), an amino ($NR_2$), a nitro, a sulfonate ($SO_2OR$), or a C1-C10 organic group, wherein each R is independently a hydrogen or an organic group.

In one embodiment, the phenylpropanoid substrate includes a coumarin structure, such as umbelliferone. In one embodiment, the phenylpropanoid substrate includes a stilbene structure, such as reserveratrol. In one embodiment, the phenylpropanoid substrate includes a flavonoid structure, such as naringenin.

In one embodiment, the microbe is E. coli. In one embodiment, the HpaBC activity is endogenous to the microbial cell. In one embodiment, the microbe is a genetically engineered cell including greater HpaBC activity than a control microbe.

Also provided herein is a genetically engineered microbe that has greater HpaBC activity than a control microbe. In one embodiment, the genetically engineered microbe includes an exogenous coding regions encoding HpaB or HpaC. In one embodiment, the genetically engineered microbe includes exogenous coding regions encoding HpaB and HpaC As used herein, the term "protein" refers broadly to a polymer of two or more amino acids joined together by peptide bonds. The term "protein" also includes molecules which contain more than one polypeptide joined by a disulfide bond, or complexes of proteins that are joined together, covalently or noncovalently, as multimers (e.g., dimers, tetramers). Thus, the terms peptide, oligopeptide, and polypeptide are all included within the definition of protein and these terms are used interchangeably.

As used herein, a protein may be "structurally similar" to a reference protein if the amino acid sequence of the protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

As used herein, the term "polynucleotide" refers to a polymeric form of nucleotides of any length, either ribonucleotides, deoxynucleotides, peptide nucleic acids, or a combination thereof, and includes both single-stranded molecules and double-stranded duplexes. A polynucleotide can be obtained directly from a natural source, or can be prepared with the aid of recombinant, enzymatic, or chemical techniques. In one embodiment, a polynucleotide is isolated.

As used herein, an "isolated" substance is one that has been removed from a cell and many of the polypeptides, nucleic acids, and other cellular material of its natural environment are no longer present. For instance, a protein, a polynucleotide, or an ortho-hydroxylated phenylpropanoid can be isolated. A substance may be purified, i.e., at least 60% free, at least 75% free, or at least 90% free from other components with which they are naturally associated. Proteins and polynucleotides that are produced by recombinant, enzymatic, or chemical techniques are considered to be isolated and purified by definition, since they were never present in a cell.

A "regulatory sequence" is a nucleotide sequence that regulates expression of a coding sequence to which it is operably linked. Nonlimiting examples of regulatory sequences include promoters, enhancers, transcription initiation sites, translation start sites, translation stop sites, transcription terminators, and poly(A) signals. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

As used herein, the term "exogenous protein" and "exogenous polynucleotide" refer to a protein or polynucleotide, respectively, which is not normally or naturally found in a microbe. As used herein, the terms "endogenous protein" and "endogenous polynucleotide" refer to a protein or polynucleotide that is normally or naturally found in a cell microbe. An "endogenous polynucleotide" is also referred to as a "native polynucleotide."

Conditions that are "suitable" for an event to occur, or "suitable" conditions are conditions that do not prevent such events from occurring. Thus, these conditions permit, enhance, facilitate, and/or are conducive to the event.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The description of the present invention exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Verified and potential substrates of HpaBC. The asterisk mark indicates the hydroxylation position.

FIG. 13. Amino acid sequence of SEQ ID NO:1 and SEQ ID NO:2.

DETAILED DESCRIPTION OF ILLUSTRATIVE EMBODIMENTS

Figure 2:
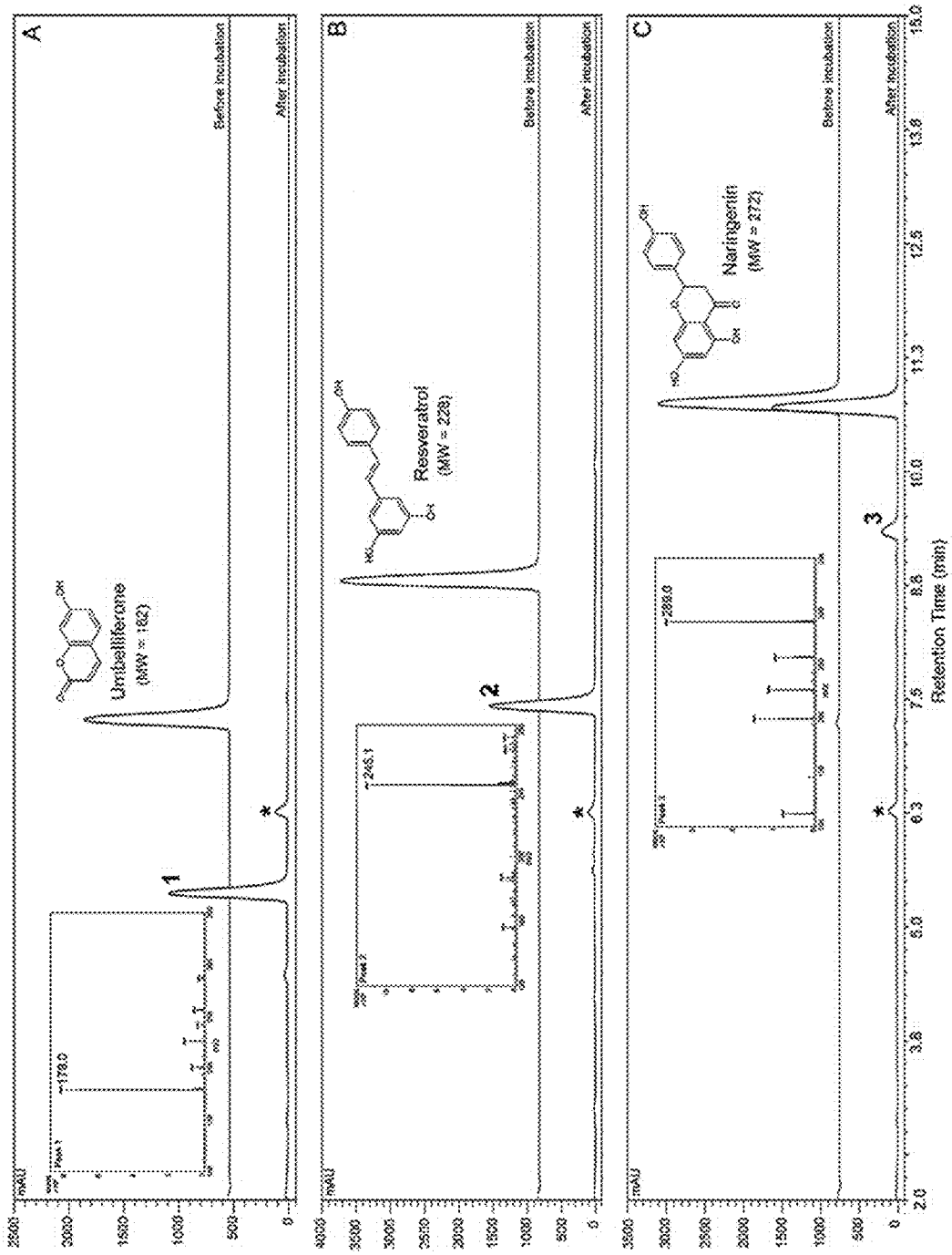
FIG. 2. HPLC chromatograms of umbelliferone, Resveratrol, and naringenin before (upper trace) and after (lower trace) incubation with the E. coli strain over-expressing HpaBC. Newly generated peaks 1, 2 and 3 reflected the major products. Asterisks indicate an unknown compound that appeared in the cultures. ESI-mass spectra are shown beside the new peaks.

Provided herein are methods for hydroxylating a phenylpropanoid substrate to produce an ortho-hydroxylated phenylpropanoid. As used herein, a "phenylpropanoid" is a compound that includes a first six-carbon ring and further includes at least one additional cyclic structure.

In one embodiment, the phenylpropanoid substrate has the formula

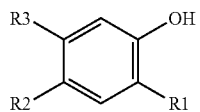

where R1 is the ortho-position a hydroxyl group is added when using the methods described herein. The ortho-position is relative to the hydroxyl group present on the formula above, i.e., a phenylpropanoid substrate is hydroxylated at a position next to a hydroxyl group present on the phenylpropanoid substrate as shown above.

In one embodiment R2 is a divalent organic linking group, wherein one end of the linking group is bound to the first six-carbon ring and the other end of the linking group is bound to an additional cyclic structure. As used herein, the terms "organic linking group" and "organic group" are used for the purpose of the methods disclosed herein to mean a hydrocarbon group that is classified as an aliphatic group. In the context of the embodiments described herein, the term "aliphatic group" means a saturated or unsaturated linear or branched hydrocarbon group. The number of carbons in the divalent linking group may be, may be at least, or may be no greater than 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. The divalent linking group may include one or more olefinically unsaturated groups (i.e., carbon-carbon double bonds), one or more carbon-carbon triple bonds, or a combination of single, double, and/or triple bonds.

As used herein, the term "cyclic structure" refers to a ring structure where the ring is made up of five atoms or six atoms. In one embodiment, the additional cyclic structure may be a benzene ring or a cyclopentane. In one embodiment, the additional cyclic structure may be a heterocycle, where the heterocycle is a structure of five atoms or six atoms making up the closed ring, and at least one of the atoms of the ring is a heteroatom. The heteroatom may be a nitrogen, oxygen, or sulfur. The additional cyclic structure may be attached to the divalent organic group at a carbon of the cyclic structure or at a heteroatom of the additional cyclic structure.

The R3 may be a hydrogen, or may be a nonring substituent. For instance, R3 may be, but is not limited to, halogen (e.g., F, Cl, Br, I), nitrile (CN), hydroxy (OH), alkoxy (OR, including carbonyl), nitrate (O—NO$_2$), nitrite (O—N=O), sulfate (O—SO$_3$R), amino (NR$_2$), nitro (NO$_2$), sulfonate (SO$_2$OR), or a C1-C10 organic group (e.g., in some embodiments a C1-C4 organic group or moiety), with each R independently being hydrogen or an organic group.

In one embodiment R2 is joined to R3 to form the additional cyclic structure. The atom of the additional cyclic structure that is bound to the first six-ring structure at the R3 position may be a carbon or may be a heteroatom of the additional cyclic structure.

The divalent organic linking group and the additional cyclic structure can optionally be substituted with nonring substituents. The skilled person will recognize that the hydrogen atom on one or more of the hydrogen-bearing carbon atoms in the additional cyclic structure may be substituted with a substituent including, but not limited to, halogen (e.g., F, Cl, Br, I), nitrile (CN), hydroxy (OH), alkoxy (OR, including carbonyl), nitrate (O—NO$_2$), nitrite (O—N=O), sulfate (O—SO$_3$R), amino (NR$_2$), nitro (NO$_2$), sulfonate (SO$_2$OR), or a C1-C10 organic group (e.g., in some embodiments a C1-C4 organic group or moiety), with each R independently being hydrogen or an organic group.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups, hydroxyl groups, or other conventional substituents. Where the term "moiety" is used to describe a chemical compound or substituent, only an unsubstituted chemical material is intended to be included.

A phenylpropanoid useful as substrate in the methods described herein may include a coumarin structure:

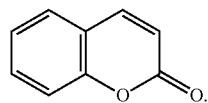

An example of a phenylpropanoid having a coumarin structure includes, but is not limited to, umbelliferone:

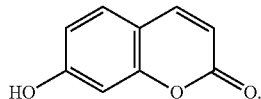 [SMILES: O=c1ccc2ccc(O)cc2o1]

Figure 4:
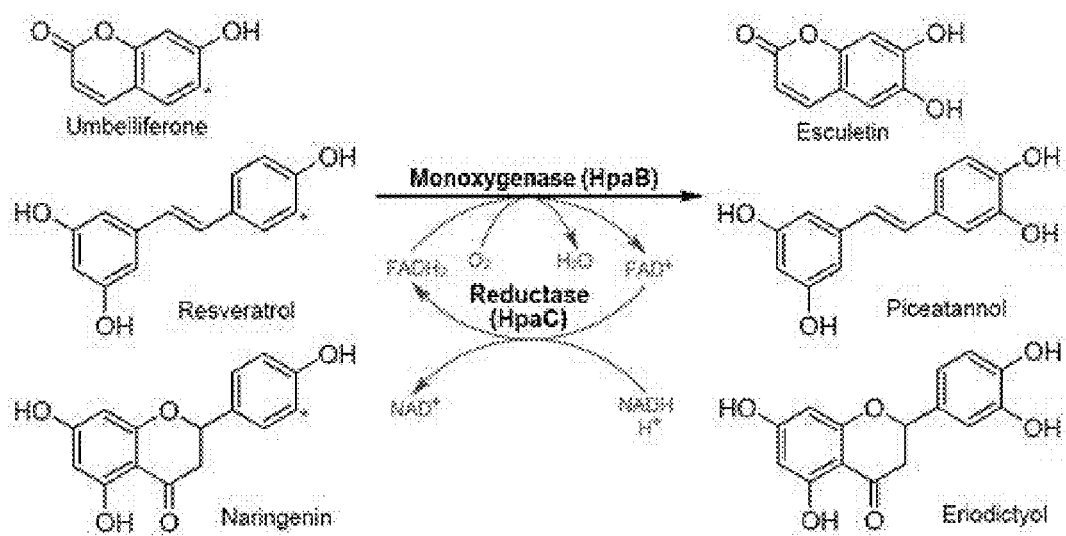
FIG. 4. Ortho-hydroxylation of phenylpropanoids by HpaBC.

The ortho-hydroxylation of umbelliferone by HpaBC results in esculetin (see FIG. 4).

A phenylpropanoid useful as substrate in the methods described herein may include a stillbene structure that is either a trans-isomer or a cis-isomer. An example of a trans-isomer of stillbene is:

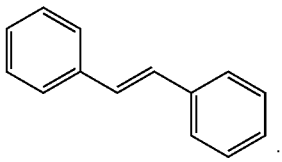 [SMILES: C(=C\c1ccccc1)/c1ccccc1]

An example of a phenylpropanoid having a stillbene structure includes, but is not limited to, resveratrol:

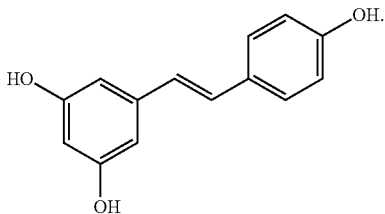 [SMILES: Oc1ccc(/C=C/c2cc(O)cc(O)c2)cc1]

The ortho-hydroxylation of resveratrol by HpaBC results in piceatannol (see FIG. 4).

A phenylpropanoid useful as substrate in the methods described herein may include a flavonoid structure. In one embodiment, a flavonoid structure may be a flavone, such as

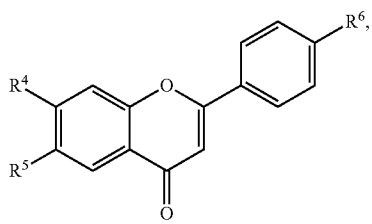

where the flavone is hydroxylated at R4, R5, and/or R6.

An example of a phenylpropanoid having a flavone structure includes, but is not limited to, naringenin:

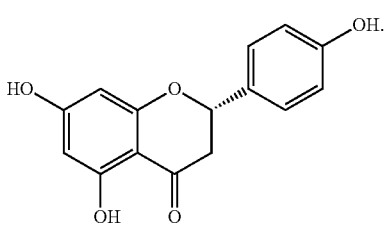 [SMILES: O=C1C[C@@H](c2ccc(O)cc2)Oc2cc(O)cc(O)c21]

The ortho-hydroxylation of naringenin by HpaBC results in eriodictyol (see FIG. 4).

In one embodiment, a flavonoid structure may be an isoflavan, such as

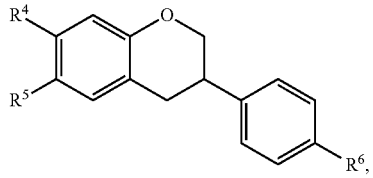

where the isoflavin is hydroxylated at R4, R5, and/or R6.

In one embodiment, a flavonoid structure may be a neoflavonoid, such as

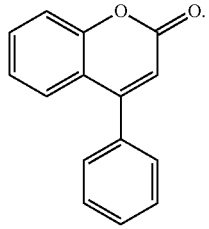 [SMILES: O=c1cc(-c2ccccc2)c2ccccc2o1]

In the context of the embodiments described herein, suitable organic groups for compounds described herein are those that do not interfere with the ortho-hydroxylation of a phenylpropanoid substrate. For instance, in one embodiment a suitable organic group does not interfere with the ability of the phenylpropanoid substrate to fit into the catalytic pocket of HpaB.

The reaction described herein to ortho-hydroxylate a phenylpropanoid substrate is catalyzed by a two component non-P450 hydroxylase (HpaBC) that catalyzes the hydroxylation of 4-hydroxyphenylacetate (4HPA) into 3,4-dihydroxyphenylacetate, the first enzymatic step of 4HPA degradation in *E. coli*. The large component (HpaB) has been characterized as an FADH2-utilizing monooxygenase (Xun and Sandvik, *Appl. Environ. Microbiol.*, 2000, 66, 481-486), while the small component (HpaC) is an NAD(P)H-flavin oxidoreductase that acts as a coupling factor and supplies FADH2 to HpaB (Louie et al., *Biochemistry (Most.)*, 2003, 42, 7509-7517). HpaBC was reported to have a broad substrate range and can act on a series of 4HPA analogs such as phenol, p-cresol and tyrosine (Prieto et al., *J. Bacteriol.*, 1993, 175, 2162-2167), and has recently been found to also selectively hydroxylate a simple phenylpropanoid compound, p-coumaric acid to form caffeic acid (Lin and Yan, *Microb Cell Fact*, 2012, 11, 42; Yan and Lin, US Patent Application Publication 20130130340).

An example of an HpaB protein includes, but is not limited to, the sequence depicted at SEQ ID NO:1 (GenBank number CAA82321.1). An example of an HpaC protein includes, but is not limited to, the sequence depicted at SEQ ID NO:2 (GenBank number CAA82322.2). A coding region encoding an HpaB and/or an HpaC may be obtained from a suitable biological source, such as a microbial cell, using standard molecular cloning techniques. For example, coding regions may be isolated using polymerase chain reaction (PCR) with primers designed by standard primer design software which is commonly used in the art. Exemplary primers for use in isolating a coding region encoding an HpaB and/or an HpaC from a microbial cell are readily available (see Lin and Yan, *Microb Cell Fact*, 2012, 11, 42; Yan and Lin, US Patent Application Publication 20130130340; and Xun and Sandvik, *Appl. Environ. Microbiol.*, 2000, 66, 481-486). Suitable microbes that may harbor useful HpaB and HpaC coding regions include, but are not limited to, *E. coli, Pseudomonas* spp., and *Thermus thermophilus*. The cloned sequences are easily ligated into any standard expression vector by the skilled person.

Other examples of HpaB and HpaC proteins include those that are structurally similar to the amino acid sequence of SEQ ID NO:1 or SEQ ID NO:2, respectively. An HpaB or an HpaC protein that is structurally similar to the amino acid sequence of SEQ ID NO:1 or SEQ ID NO:2, respectively, has HpaBC activity. HpaBC activity is the ability to ortho-hydroxylate umbelliferone to produce esculetin and ortho-hydroxylate resveratrol to produce piceatannol. In vitro and in vivo methods for testing whether a two component enzyme has HpaBC activity are described below.

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein. A candidate protein is the protein being compared to the reference protein. A candidate protein may be isolated, for example, from a microbe, or can be produced using recombinant techniques, or chemically or enzymatically synthesized.

Unless modified as otherwise described herein, a pairwise comparison analysis of amino acid sequences can be carried out using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on. Alternatively, polypeptides may be compared using the BESTFIT algorithm in the GCG package (version 10.2, Madison Wis.).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein described herein may be selected from other members of the class to which the amino acid belongs. For example, it is known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$.

Thus, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence.

Alternatively, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

An HpaBC two component enzyme has HpaBC activity. Whether two proteins act together to have HpaBC activity can be determined by measuring the ability of a two component enzyme to convert umbelliferone to esculetin or resveratrol to piceatannol (see FIG. 4). Methods for measuring the production of esculetin or piceatannol from the appropriate substrate are described in Example 1. In one embodiment, an isolated HpaBC two component enzyme used in an in vitro enzyme assay has specific kinetic parameters towards the substrates umbelliferone, resveratrol, and its natural substrate 4-hydroxyphenylacetate (4-HPA) as shown in Table 1 in Example 1.

An HpaB and/or an HpaC protein may include other amino acid residues. In one embodiment, the additional amino acids are heterologous amino acids. As used herein, "heterologous amino acids" refers to amino acids that are not normally or naturally found flanking the sequence depicted at, for instance, SEQ ID NO:1 or SEQ ID NO:2 in a microbial cell. A protein that includes, for instance, SEQ ID NO:1 or SEQ ID NO:2 and heterologous amino acids may be referred to as a fusion polypeptide.

In one embodiment, the additional amino acid sequence may be useful for purification of the fusion polypeptide by affinity chromatography. Various methods are available for the addition of such affinity purification moieties to proteins. Representative examples include, for instance, polyhistidine-tag (His-tag) and maltose-binding protein (see, for instance, Hopp et al. (U.S. Pat. No. 4,703,004), Hopp et al. (U.S. Pat. No. 4,782,137), Sgarlato (U.S. Pat. No. 5,935,824), and Sharma (U.S. Pat. No. 5,594,115)). In one embodiment, the additional amino acid sequence may be a carrier polypeptide. The carrier polypeptide may be used to increase the immunogenicity of the fusion polypeptide to increase production of antibodies that specifically bind to a protein described herein. In another embodiment, the additional amino acid sequence may be a fluorescent polypeptide (e.g., green, yellow, blue, or red fluorescent proteins) or other amino acid sequences that can be detected in a cell or in vitro. If a protein described herein includes an additional amino acid sequence not normally or naturally associated with the polypeptide, the additional amino acids are not considered when percent structural similarity to a reference amino acid sequence is determined.

Polypeptides described herein can be produced using recombinant DNA techniques, such as an expression vector present in a cell. Such methods are routine and known in the art. The polypeptides may also be synthesized in vitro, e.g., by solid phase peptide synthetic methods. The solid phase peptide synthetic methods are routine and known in the art.

A polypeptide produced using recombinant techniques or by solid phase peptide synthetic methods can be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity.

Also provided are polynucleotides encoding an HpaB or an HpaC protein. Given the amino acid sequence of an HpaB or an HpaC protein described herein, a person of ordinary skill in the art can determine the full scope of polynucleotides that encode that amino acid sequence using conventional, routine methods. The class of nucleotide sequences encoding a selected protein sequence is large but finite, and the nucleotide sequence of each member of the class may be readily determined by one skilled in the art by reference to the standard genetic code, wherein different nucleotide triplets (codons) are known to encode the same amino acid.

An HpaB or an HpaC polynucleotide described herein may include heterologous nucleotides flanking the coding region encoding the HpaB or HpaC protein. The boundaries of a coding region are generally determined by a translation start codon at its 5' end and a translation stop codon at its 3' end. As used herein, "heterologous nucleotides" refers to a nucleotide sequence that is not normally or naturally found flanking an open reading frame in a cell encoding an HpaB or an HpaC protein. Examples of heterologous nucleotides include, but are not limited to, a regulatory sequence. The number of heterologous nucleotides may be, for instance, at least 10, at least 100, or at least 1000.

A polynucleotide described herein can be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989). A vector can provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and transposon vectors. A vector may be replication-proficient or replication-deficient. A vector may result in integration into a cell's genomic DNA. Typically, a vector is capable of replication in a host cell, such as *E. coli*.

Selection of a vector depends upon a variety of desired characteristics in the resulting construct, such as a selection marker, vector replication rate, and the like. Suitable host cells for cloning or expressing the vectors herein are prokaryotic or eukaryotic cells. Suitable eukaryotic cells include mammalian cells, such as murine cells and human cells. Suitable prokaryotic cells include eubacteria, such as gram-negative organisms, for example, *E. coli*.

An expression vector optionally includes regulatory sequences operably linked to a polynucleotide encoding HpaB or HpaC. An example of a regulatory sequence is a promoter. A promoter may be functional in a host cell used, for instance, in the construction and/or characterization of a polynucleotide encoding HpaB or HpaC, and/or may be functional in the ultimate recipient of the vector. A promoter may be inducible, repressible, or constitutive, and examples of each type are known in the art. A polynucleotide encoding a protein described herein may also include a transcription terminator. Suitable transcription terminators are known in the art. In one embodiment, a polynucleotide encoding an HpaB and a polynucleotide encoding an HpaC may be expressed as an operon, e.g., a single promoter drives expression of both coding regions.

Polynucleotides described herein can be produced in vitro or in vivo. For instance, methods for in vitro synthesis include, but are not limited to, chemical synthesis with a conventional DNA/RNA synthesizer. Commercial suppliers of synthetic polynucleotides and reagents for in vitro synthesis are known. Methods for in vitro synthesis also include, for instance, in vitro transcription using a circular or linear expression vector in a cell free system. Expression vectors can also be used to produce a polynucleotide of the present invention in a cell, and the polynucleotide may then be isolated from the cell.

The coding regions encoding an HpaB and/or HpaC protein may be introduced into a microbial cell using genetic engineering techniques. The term "microbe" is used interchangeably with the term "microorganism" and means any microscopic organism existing as a single cell, cell clusters, or multicellular relatively complex organisms. While certain embodiments are described using *E. coli*, the microbes and methods of use are not limited to *E. coli* and there are a number of other options for microbes suitable for engineering to ortho-hydroxylate a substrate and for use in the methods described herein. The suitable microbial hosts for the ortho-hydroxylation of a substrate as described herein include, but are not limited to, a wide variety of bacteria, archaea, and yeast including members of the genera *Escherichia* (such as *E. coli*), *Pseudomonas* spp. (such as *P. putida*), *Thermus thermophilus*, *Salmonella*, *Clostridium*, *Zymomonas*, *Bacillus* (such as *B. subtilis* and *B. licheniformis*), *Rhodococcus* (such as *R. erythropolis*), *Alcaligenes* (such as *A. eutrophus*), *Klebsiella*, *Paenibacillus* (such as *P. macerans*), *Lactobacillus* (such as *L. plantarum*), *Enterococcus* (such as *E. gallinarium*, *E. faecalis*, and *E. faecium*), *Arthrobacter*, *Brevibacterium*, *Corynebacterium Candida*, *Hansenula*, *Pichia* and *Saccharomyces* (such as *S. cerevisiae*). Other suitable microbial hosts include algae, protozoa, microscopic plants such as green algae, and microscopic animals such as rotifers and planarians. If necessary, a coding region encoding an enzyme described herein can be modified using routine methods to reflect the codon usage bias of a microbial host cell to optimize expression of a polypeptide.

A cell that has been genetically engineered to express HpaB and/or HpaC for the ortho-hydroxylation of an appropriate substrate may be referred to as a "host" cell, a "recombinant" cell, a "metabolically engineered" cell, a "genetically engineered" cell or simply an "engineered" cell. These and similar terms are used interchangeably. A genetically engineered cell refers to a microbe that has been altered by the hand of man by the introduction of at least one exogenous polynucleotide. Thus, in one embodiment, a genetically engineered cell contains one or more exogenous polynucleotides which have been created through standard molecular cloning techniques to bring together genetic material that is not natively found together. For example, a microbe is a genetically engineered microbe by virtue of introduction of an exogenous polynucleotide. "Engineered" also includes a microbe that has been genetically manipulated such that one or more endogenous nucleotides have been altered. For example, a microbe is an engineered microbe by virtue of introduction of an alteration of endogenous nucleotides into a suitable microbe. For instance, a regulatory region, such as a promoter, could be altered to result in increased or decreased expression of an operably linked endogenous coding region. DNA sequences used in the construction of recombinant DNA molecules can originate from any species. For example, bacterial DNA may be joined with fungal DNA. Alternatively, DNA sequences that do not occur anywhere in nature may be created by the chemical synthesis of DNA, and incorporated into recombinant molecules. Proteins that result from the expression of recombinant DNA are often termed recombinant proteins. Examples of recombination may include inserting foreign polynucleotides into a cell, inserting synthetic polynucleotides into a cell, or relocating or rearranging polynucleotides within a cell. Any form of recombination may be considered to be genetic engineering and therefore any recombinant cell may also be considered to be a genetically engineered cell. A genetically engineered microbe has greater levels of HpaBC activity than a control microbe.

Genetically engineered cells are also referred to as "metabolically engineered" cells when the genetic engineering modifies or alters one or more particular metabolic pathways so as to cause a change in metabolism. The goal of metabolic engineering is to improve the rate and conversion of a substrate into a desired product. General laboratory methods for introducing and expressing or overexpressing native and normative proteins such as enzymes in many different cell types (including bacteria, archaea, and yeasts,) are routine and known in the art; see, e.g., Sambrook et al, *Molecular Cloning: A Laboratory Manual.*, Cold Spring Harbor Laboratory Press (1989), and *Methods for General and Molecular Bacteriology*, (eds. Gerhardt et al.) American Society for Microbiology, chapters 13-14 and 16-18 (1994).

The introduction of coding regions encoding an HpaB and/or an HpaC into a cell involves expression or overexpression of one or both of the enzymes. An enzyme is "overexpressed" in a recombinant cell when the enzyme is expressed at a level higher than the level at which it is expressed in a comparable wild-type cell. In cells that do not express a particular endogenous enzyme, or in cells in which the enzyme is not endogenous (i.e., the enzyme is not native to the cell), any level of expression of that enzyme in the cell is deemed an "overexpression" of that enzyme for purposes of the present invention.

As will be appreciated by a person of skill in the art, overexpression of an enzyme can be achieved through a number of molecular biology techniques. For example, overexpression can be achieved by introducing into the host cell one or more copies of a polynucleotide encoding the desired enzyme. The polynucleotide encoding the desired enzyme may be endogenous or exogenous to the host cell. Typically, the polynucleotide is introduced into the cell using a vector. The polynucleotide may be circular or linear, single-stranded or double stranded, and can be DNA, RNA, or any modification or combination thereof. The vector can be any molecule that may be used as a vehicle to transfer genetic material into a cell. Examples of molecular biology techniques used to transfer nucleotide sequences into a microorganism include, without limitation, transfection, electroporation, transduction, and transformation. These methods are routine and known in the art. Insertion of a vector into a target cell is usually called transformation for bacterial cells and transfection for eukaryotic cells, however insertion of a viral vector is often called transduction. The terms transformation, transfection, and transduction, for the purpose of the present invention, are used interchangeably herein.

Also provided herein are methods for producing an ortho-hydroxylated phenylpropanoid using the HpaBC proteins described herein. The method includes exposing a suitable phenylpropanoid substrate to an HpaBC two component enzyme. In one embodiment, the method includes culturing a microbe that includes HpaBC proteins in the presence of a phenylpropanoid substrate under conditions suitable to ortho-hydroxylate the phenylpropanoid substrate. The cell may be one expressing an endogenous HpaB, an endogenous HpaC, or both HpaB and HpaC. Whether a cell has endogenous HpaBC activity can be easily determined by the skilled person using methods that are known in the art and routine. Examples of microbes having endogenous HpaBC activity include, for instance, *E. coli, Pseudomonas* spp., and *Thermus thermophilus*. Alternatively, the cell may be a recombinant cell that expresses HpaB and HpaC at a level greater than a control cell. The phenylpropanoid substrate may be produced by the cell, or may be added to the culture that includes the microbe.

In one embodiment, the method includes incubating isolated HpaBC proteins with a phenylpropanoid substrate under conditions suitable to ortho-hydroxylate the phenylpropanoid substrate. The isolated HpaBC proteins may be obtained from a cell expressing an endogenous HpaB, an endogenous HpaC, or both HpaB and HpaC. The cell used as a source of the HpaBC proteins may be a recombinant cell that expresses HpaB and HpaC at a level greater than a control cell. Alternatively, the HpaBC may be produced chemically or synthetically.

The ortho-hydroxylatd phenylpropanoid produced by the cells can be isolated and optionally purified from the cell. It can be isolated directly from the cells, or from the culture medium, for example, during a fermentation process. Isolation and/or purification can be accomplished using known and routine methods. The ortho-hydroxylatd phenylpropanoid may be used in any application, including pharmaceutical uses, such as anti-aging, anti-inflammatory, anti-cancer, and anti-parasitic activity, inhibition of adipogenesis, and induction of apoptosis of maturing preadipocytes.

In various embodiments different supplements may be included. For instance, when the phenylpropanoid is ortho-hydroxylated in vivo (in a cell) or in vitro (in a cell free environment), the medium may be supplemented with $FADH_2$, $FAD^+$, $NAD^+$, and/or NADH. In some embodiments, such as when aerobic conditions are used, a reducing agent may be included to decrease the oxidation of the ortho-hydroxylated phenylpropanoids produced. Examples of appropriate reducing agents include, but are not limited to, ascorbic acid.

The cells can be cultured aerobically or anaerobically, or in a multiple phase fermentation that makes use of periods of anaerobic and aerobic fermentation. Batch fermentation, continuous fermentation, or any other fermentation method may be used.

The present invention is illustrated by the following examples. It is to be understood that the particular examples, materials, amounts, and procedures are to be interpreted broadly in accordance with the scope and spirit of the invention as set forth herein.

EXAMPLE 1

A promiscuous non-P450 monooxygenase (HpaBC) from *Escherichia coli* was identified to catalyze ortho-hydroxylation of plant phenylpropanoids umbelliferone, resveratrol, and naringenin. Whole-cell biocatalysis afforded the generation of the pharmaceutically important compounds esculetin and piceatannnol with high yields (~100%) and high titers, demonstrating a promising biocatalytic hydroxylation platform for scale-up applications.

Strains, Plasmids and Media.

*E. coli* strain XL1-Blue was used for plasmid construction and propagation. *E. coli* strain BW25113 containing F' from XL1-Blue was used for protein over-expression and whole-cell biocatalysis. Plasmid pZE12-luc was used for gene over-expression in *E. coli* (Lin and Yan, 2012. Microb Cell Fact 11(1):42). Luria-Bertani (LB) medium was used for growing *E. coli* cells during gene cloning, plasmid propagation, and inoculum preparation; while the whole-cell biocatalysis was performed in modified M9 medium (M9Y) containing (per liter): glycerol (20 g), glucose (2.5 g), yeast extract (5 g), $NH_4Cl$ (1 g), $Na_2HPO_4$ (6 g), $KH_2PO_4$ (3 g), NaCl (0.5 g), $MgSO_4 \cdot 7H_2O$ (1 mmol), and $CaCl_2 \cdot 2H_2O$ (0.1 mmol). For the strains carrying pZE12-luc derived plasmids, ampicillin was supplemented into the medium to a final concentration of 100 µg/ml.

Construction of Plasmids.

The plasmid pZE-HpaBC carrying *E. coli* genes hpaB and hpaC was constructed in our previous work (Lin and Yan, 2012. Microb Cell Fact 11(1):42). pZE-His7HpaB and pZE-His 7HpaC were constructed for the over-expression and purification of HpaB and HpaC, respectively. A 7-histidine tag was fused to the N-terminus of HpaB and HpaC when the genes were amplified from *E. coli* genomic DNA using the primers His HpaB-F/His HpaB-R and His HpaC-F/His HpaC-R, respectively. The amplified fragments and pZE12-luc were digested with KpnI and SphI, and then ligated by the NEB quick ligase kit. The primer sequences are listed below (the His-tag sequences are underlined).

```
HisHpaB-F:
                                        (SEQ ID NO: 3)
gggaaaggtaccatgcatcaccatcatcaccaccataa accagaagatttccgcgc HisHpaB-R:
                                        (SEQ ID NO: 4)
gggaaagcatgcttatttcagcagcttatccagcatgttg HisHpaC-F:
                                        (SEQ ID NO: 5)
gggaaaggtaccatgcatcaccatcatcaccaccatcaa ttagatgaacaacgcctgc HisHpaC-R:
                                        (SEQ ID NO: 6)
gggaaagcatgcttaaatcgcagcttccatttccagc
```

HpaBC Substrates Screening.

The *E. coli* strain harboring pZE-HpaBC was pre-inoculated into LB liquid medium containing ampicillin (100 µg/ml) and grown overnight at 37° C. Then 200 µl of the inoculum was transferred into 20 ml of fresh M9Y medium. The *E. coli* cells were grown at 37° C. till the $OD_{600}$ values reached around 0.6 and then transferred to 30° C. and induced by 0.5 mM IPTG. After 3 hours' protein expression, the substrates umbelliferone, resveratrol and naringenin were separately added into the cultures to a final concentration of 200 mg/L. After 12 hours' incubation, the cell free cultures were analyzed by HPLC.

NMR Analysis.

Figure 7:
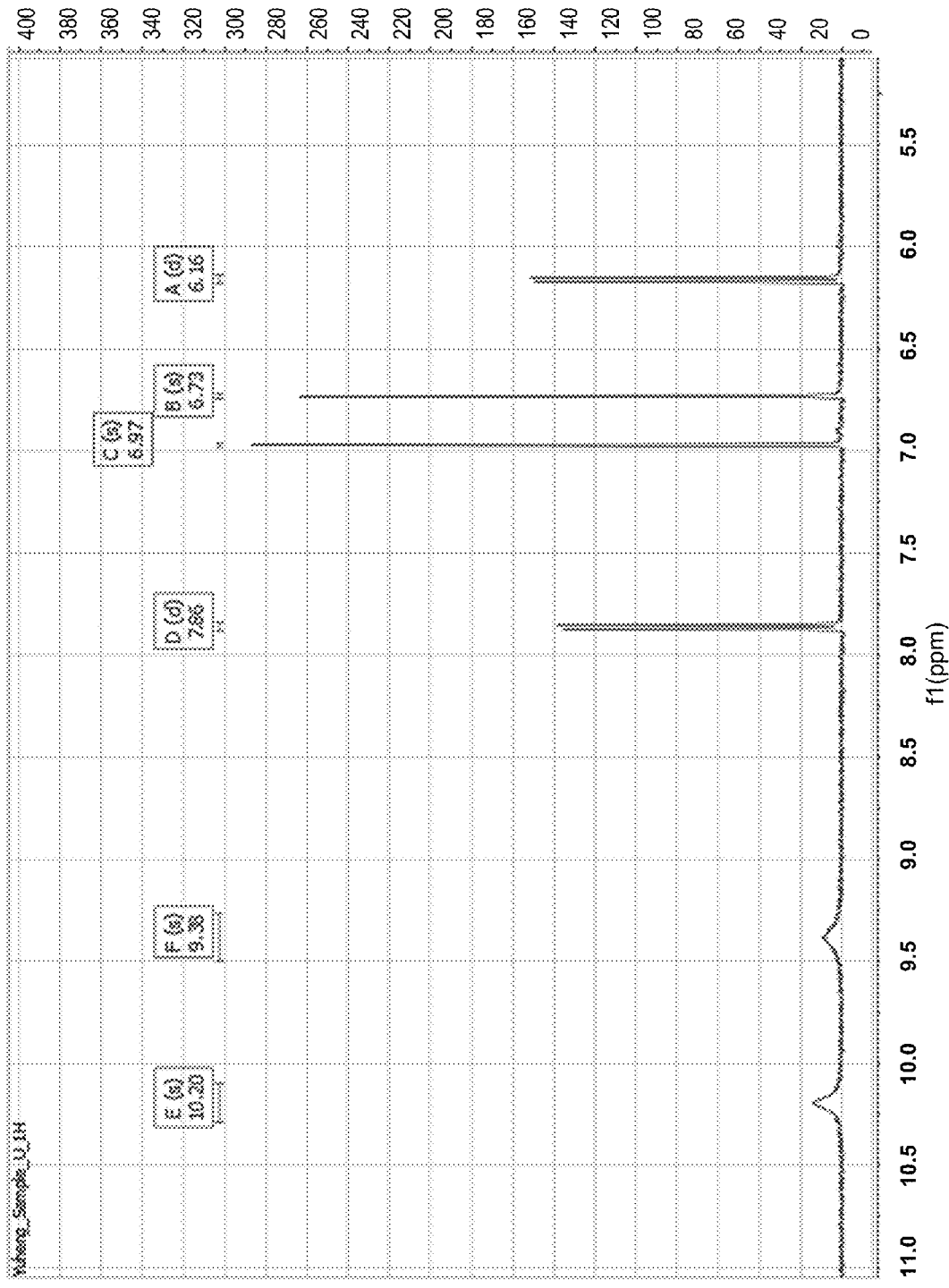
FIG. 7. $^1$H NMR spectrum of the hydroxylated umbelliferone (predicted as esculetin).
Figure 8:
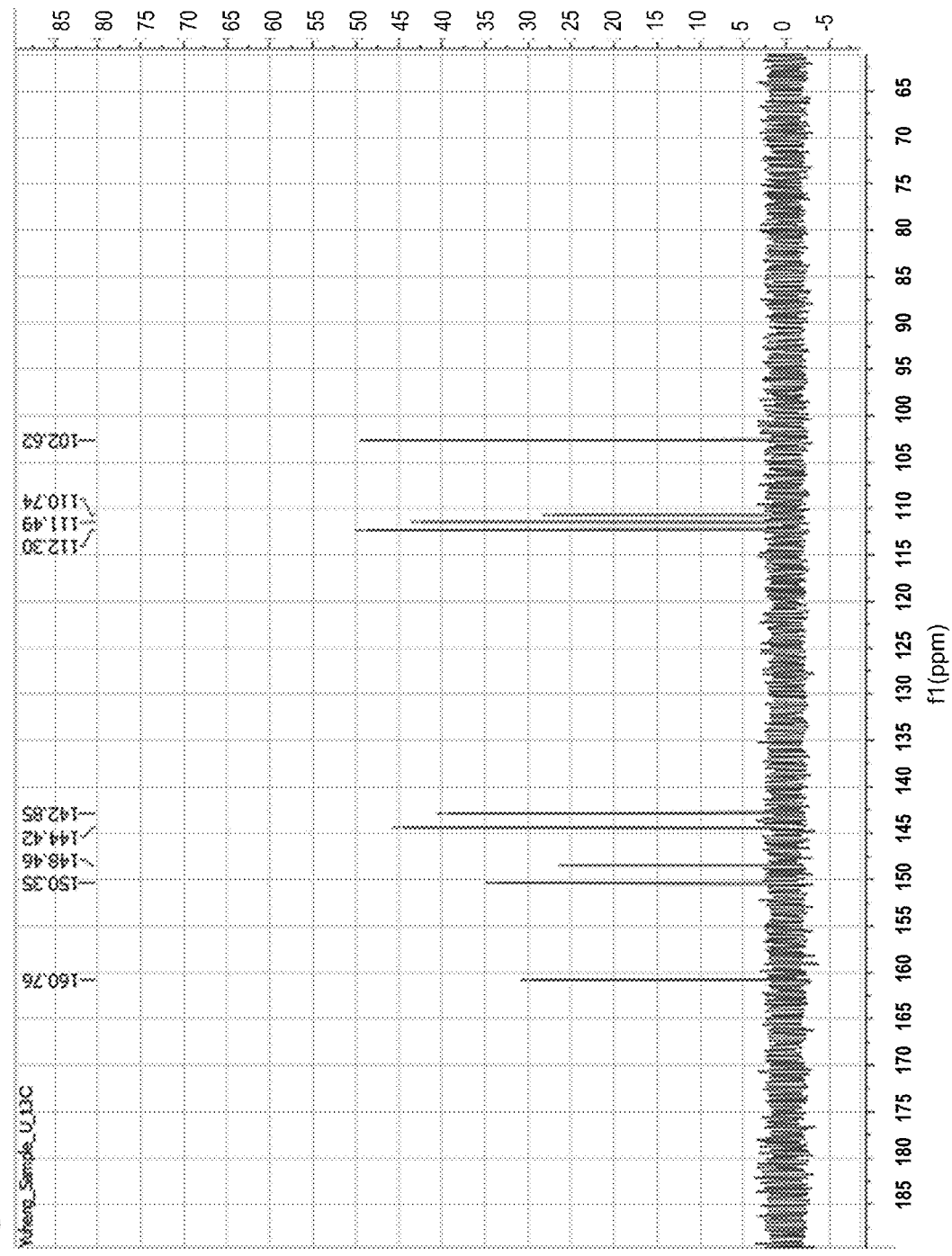
FIG. 8. $^{13}$C NMR spectrum of the hydroxylated umbelliferone (predicted as esculetin).
Figure 9:
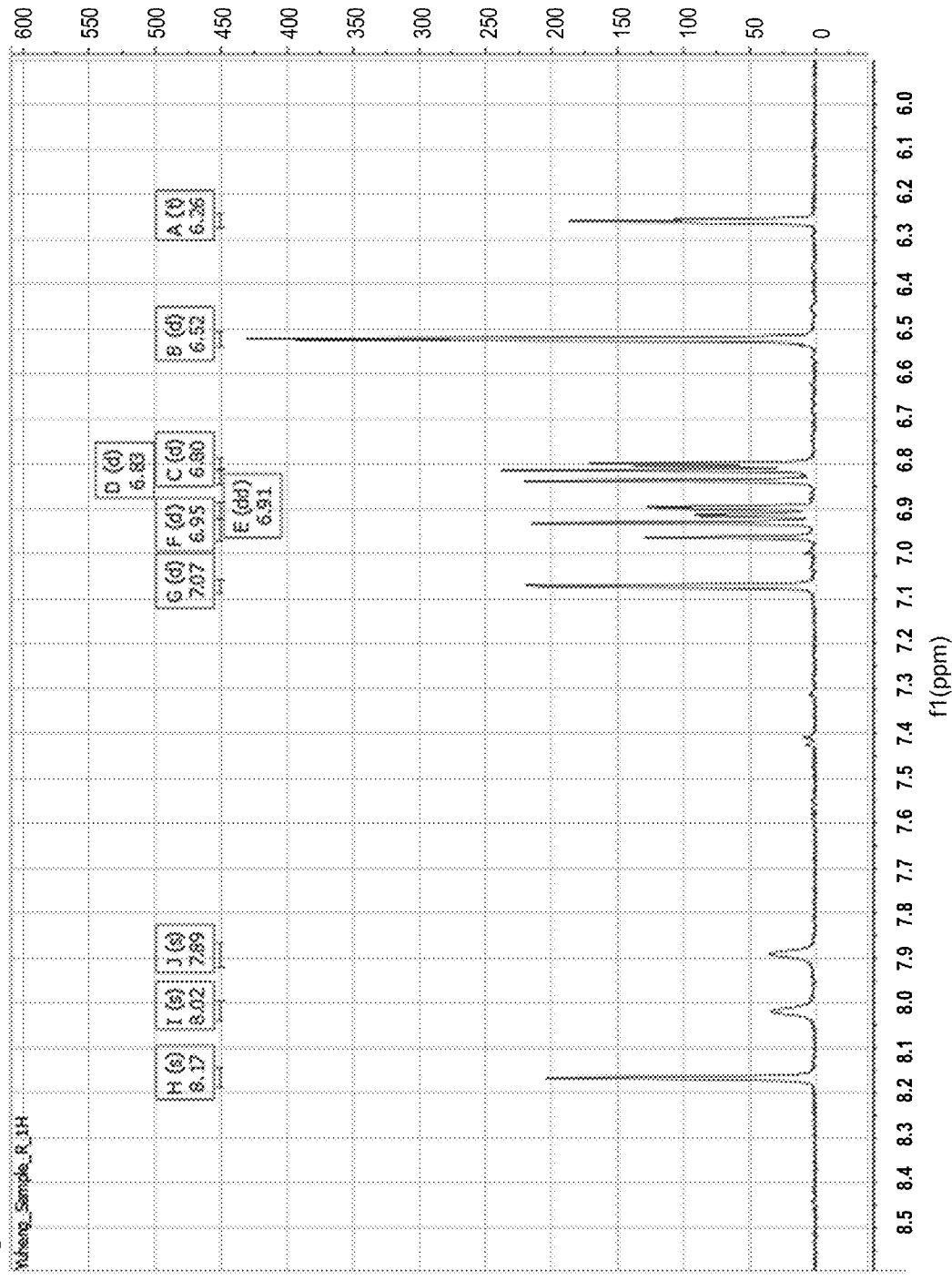
FIG. 9. $^1$H NMR spectrum of the hydroxylated resveratrol (predicted as piceatannol).
Figure 10:
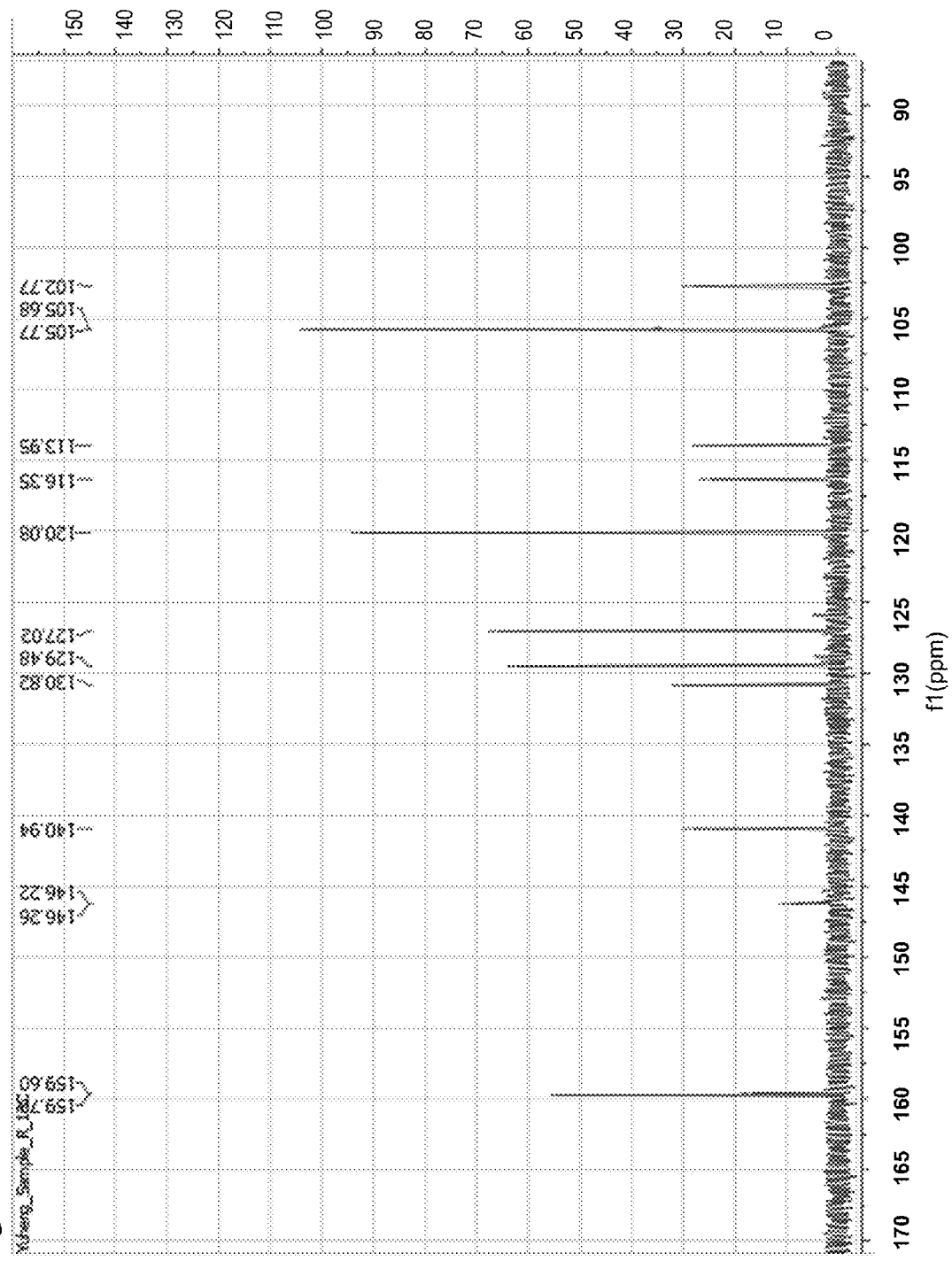
FIG. 10. $^{13}$C NMR spectrum of the hydroxylated resveratrol (predicted as piceatannol).
Figure 11:
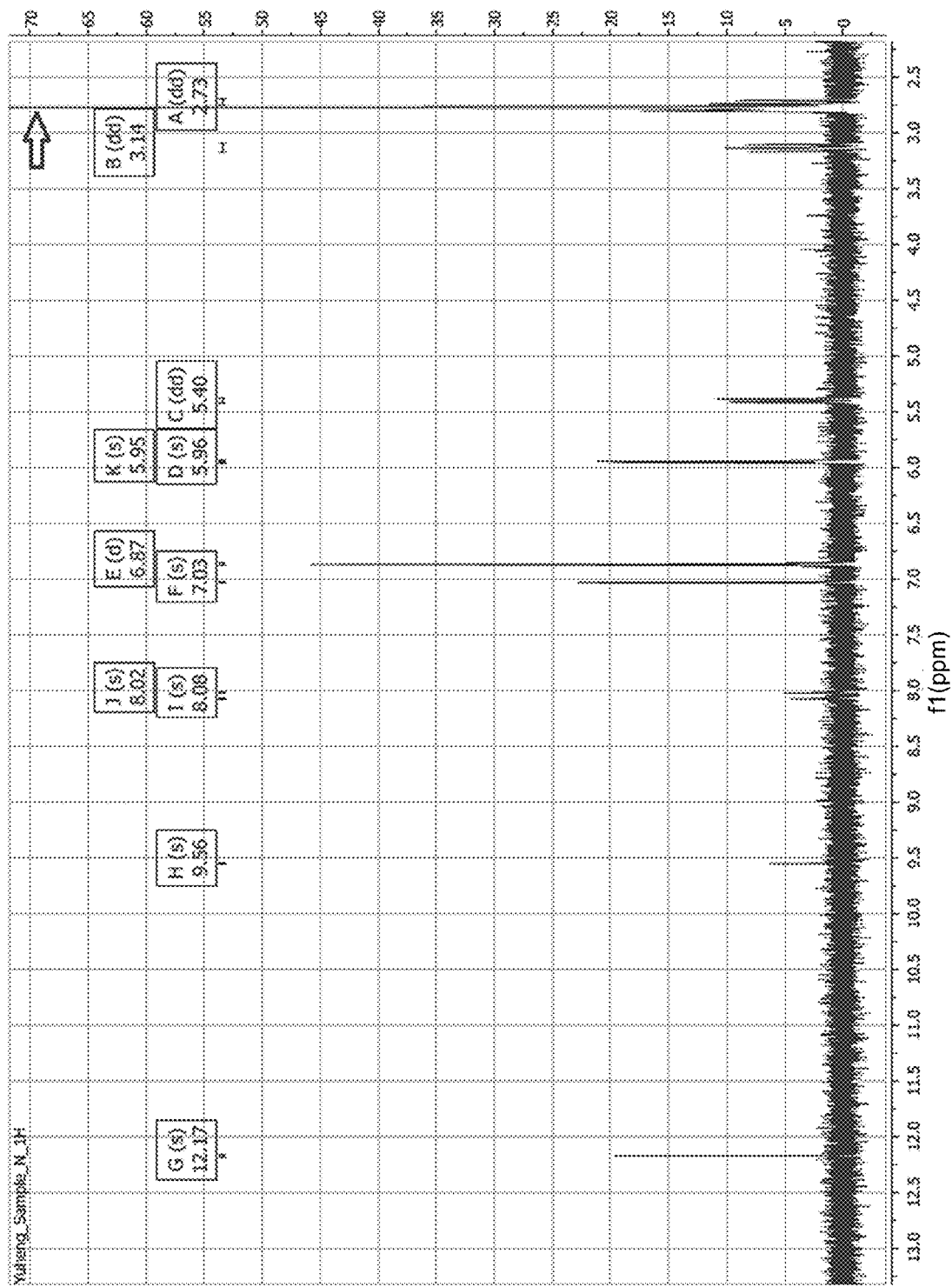
FIG. 11. $^1$H NMR spectrum of the hydroxylated naringenin (predicted as eriodictyol). The arrow indicates a peak from unknown impurities.
Figure 12:
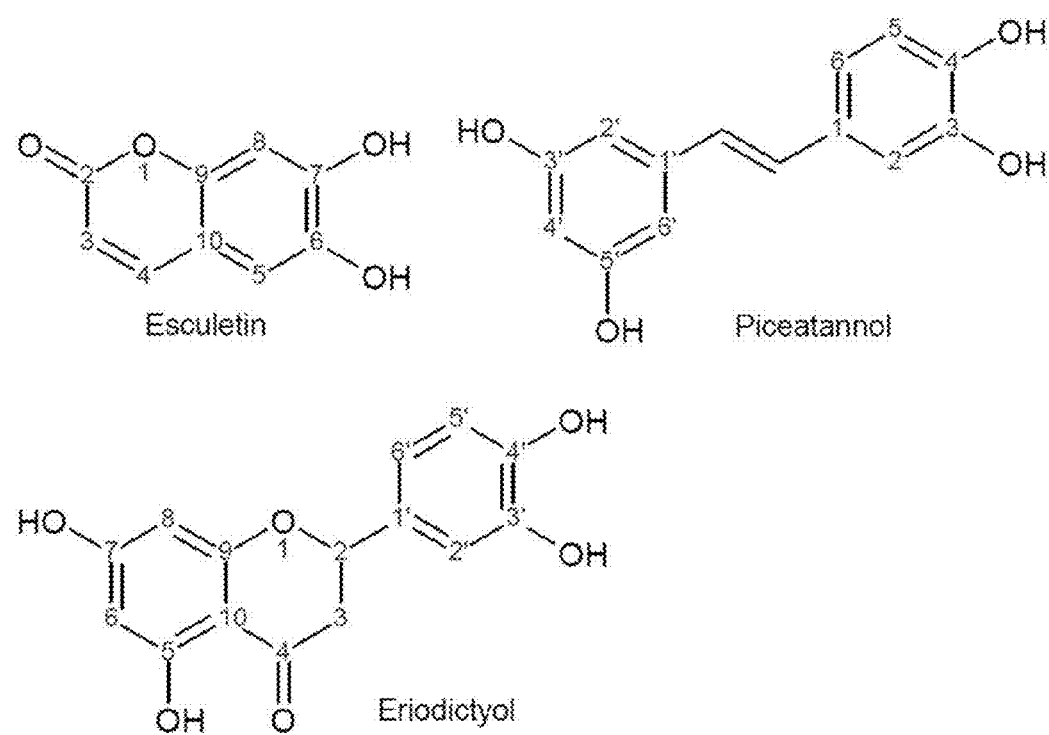
FIG. 12. Ring numbering of esculetin, piceatannol, and eriodictyol.

The produced compounds were extracted from the cultures by the same volume of acetyl acetate. Then the extracts were dried by a vacuum evaporator and re-dissolved by DMSO. Further purification was performed by collecting the product peaks using HPLC. The pure samples were obtained by acetyl acetate extraction and drying again. The NMR was run using 500-MHz Varian Unity Inova with a 5 mm Broad Band Detection Probe at 25° C. For peak 1, $^1H$ NMR data (500 MHz, DMSO-$d_6$, FIG. 7) δ: 10.20 (br s, 1H, OH-7), 9.38 (br s, 1H, OH-6), 7.86 (d, 1H, 4-H), 6.97 (s, 1H, 5-H), 6.73 (s, 1H, 8-H), 6.16 (d, 1H, 3-H) and $^{13}C$ NMR data (125 MHz, DMSO-$d_6$, FIG. 8) δ: 160.76 (C-2), 150.35 (C-7), 148.46 (C-9), 144.42 (C-4), 142.85 (C-6), 112.30 (C-5), 111.49 (C-3), 110.74 (C-10), 102.62 (C-8) are consistent with the $^1H$ and $^{13}C$ NMR data of esculetin from SDBS (Spectral Database for Organic Compounds, SDBS No.: 23227) and previous report (Li et al., 2004. Zeitschrift Fur Naturforschung Section B-a Journal of Chemical Sciences 59(8):921-924). For peak 2, $^1H$ NMR data (500 MHz, acetone-d6, FIG. 9) δ: 6.26 (t, 1H, 4'-H), 6.52 (d, 2H, 2',6'-H), 6.80 (d, 1H, olefinic H), 6.83 (d, 1H, 5-H), 6.91 (dd, 1H, 6-H), 6.95 (d, 1H, olefinic H), 7.07 (d, 1H, 2-H), 8.17 (br s, 2H, 3'-OH and 5'-OH), 8.02 (br s, 1H, OH) and 7.89 (br s, 1H, OH) and $^{13}C$ NMR data (125 MHz, acetone-d6, FIG. 10) δ: 102.77 (C4'), 105.68 and 105.77 (C-2' and 6'), 113.95 (C-2), 116.35 (C-5), 120.08 (C-6), 127.02 (olefinic), 129.48 (olefinic), 130.82 (C-1), 140.94 (C-1'), 146.22 (C-4), 146.26 (C-3), 159.60 and 159.70 (C-3' and 5') are consistent with the previously reported $^1H$ and $^{13}C$ NMR data of piceatannol (Han et al., 2008. Bulletin of the Korean Chemical Society 29(9):1800-1802). For Peak 3, $^1H$ NMR data (500 MHz, acetone-d6, FIG. 11) δ: 5.40 (dd, 1H, 2-H), 3.14 (dd, 1H, 3a-H), 2.73 (dd, 1H, 3b-H), 5.95 and 5.96 (s, 6-H and 8-H), 7.03 (s, 1H, 2'-H), 6.87 (d, 2H, 5'-H and 6'-H), 12.17 (br s, 1H, 5-OH), 9.56, 8.02 and 8.08 (3 other OHs) are consistent with the previously reported eriodictyol NMR data (Encarnacion et al., 1999. Acta Chem Scand 53(5):375-377). Ring numbering of the compounds is shown in FIG. 12.

Protein Purification and in vitro Enzyme Assay.

The *E. coli* strain was transformed with pZE-His7HpaB and pZE-His7HpaC separately. The fresh transformants were pre-inoculated in LB medium containing 100 µg/ml ampicillin and grown at 37° C. aerobically overnight. In the following day, the pre-inoculums were transferred into 50 ml of fresh LB medium at a ratio of 1:100. The cultures were cultivated at 37° C. till the $OD_{600}$ values reached about 0.6 and then induced by 0.5 mM IPTG. After additional 6 hours for protein expression at 30° C., the cells were harvested and the proteins were purified using His-Spin Protein Miniprep™ kit (ZYMO RESEARCH) according to the manual. The BCA kit (Pierce Chemicals) was used to estimate protein concentrations. The stock concentrations of purified His HpaB and His HpaC were 73.8 and 68.3 µM, respectively. The HpaBC enzyme assays were carried out according to the protocol described by Louie et al. with minor modifications (Louie et al., 2003. Biochemistry (Mosc) 42(24):7509-17). The 1 ml reaction system contains KPi Buffer (20 mM, pH=7.0), FAD (10 µM), NADH (1 mM), HpaB (0.5 µM), HpaC (0.5 µM), substrates (from 10 to 1000 µM). The reactions were conducted at 30° C. for 1 min (for 4HPA), 10 min (for resveratrol), and 15 min (for umbelliferone) and terminated by acidification with 50 µA of HCl (20%). The reaction rates were calculated according to the product formation and substrate consumption, which were measured by HPLC. Apparent kinetic parameters were determined by non-linear regression of the Michaelis-Menten equation using OriginPro8™.

Whole-cell Biocatalysis.

The *E. coli* strain harboring pZE-HpaBC was first cultivated in 50 ml LB liquid medium at 37° C. till $OD_{600}$ values reached 0.6. Then the cells were transferred to 30° C. and induced with 0.5 mM IPTG for additional 6 hours. After that, cells were harvested, re-suspended in 15 ml M9Y medium ($OD_{600}$=9.6), and incubated in a rotary shaker at 300 rpm. Umbelliferone and resveratrol were separately supplemented into the cultures to a final concentration of 1.5 g/L. Meanwhile, 1.5 mM of ascorbic acid was added to avoid the spontaneous oxidation of substrates and products. When the substrate concentrations fell below 0.5 g/L, additional 1 g/L substrates were supplemented. Umbelliferone was added twice at 2.5 and 5.5 h, while resveratrol was added only once at 8 h. Samples were taken every few hours and analyzed by HPLC.

HPLC Analysis.

Quantitative analysis of umbelliferone, resveratrol, naringenin, esculetin, piceatannol, and eriodictyol was performed by HPLC (Dionex Ultimate 3000) equipped with a reverse-phase ZORBAX SB-C18 column and an Ultimate 3000 Photodiode Array Detector. Solvent A is water containing 0.05% trifluoroacetic acid (TFA); solvent B is acetonitrile containing 0.05% TFA. The following gradient was used at a flow rate of 1 ml/min: 10 to 70% of B for 15 min, 70 to 10% B for 1 min, and 10% B for additional 4 min.

The work described herein investigated the catalytic potential of a non-P450 hydroxylase (HpaBC) towards complex aromatic metabolites. HpaBC was initially identified as a two-component monooxygenase that catalyzes the hydroxylation of 4-hydroxyphenylacetate (4HPA) into 3,4-dihydroxyphenylacetate, the first enzymatic step of 4HPA degradation in *Escherichia coli* (Prieto and Garcia, *J. Biol. Chem.*, 1994, 269, 22823-22829). The large component (HpaB) has been characterized as an FADH2-utilizing monooxygenase (Xun and Sandvik, *Appl. Environ. Microbiol.*, 2000, 66, 481-486), while the small component (HpaC) is an NAD(P)H-flavin oxidoreductase that acts as a coupling factor and supplies FADH2 to HpaB (Louie et al., *Biochemistry (Mosc.)*, 2003, 42, 7509-7517). HpaBC was reported to have a broad substrate range and can act on a series of 4HPA analogs such as phenol, p-cresol and tyrosine (Prieto et al., *J. Bacteriol.*, 1993, 175, 2162-2167) (FIG. 1). Very recently, it was found that this enzyme can also selectively hydroxylate a simple phenylpropanoid compound, p-coumaric acid to form caffeic acid (Lin and Yan, *Microb Cell Fact*, 2012, 11, 42). Whole-cell biocatalysis afforded caffeic acid production with high yield (close to 100%) and high titer (3.82 g/L or 21.2 mM).

Umbelliferone (7-hydroxycoumatin) and resveratrol (3,5,4'-trihydroxy-trans-stilbene) were first selected as substrates to survey the plasticity of the HpaBC active site, because compared with the native substrate 4HPA umbelliferone and resveratrol are bulkier in width and length, respectively, while sharing the same phenolic moiety. As the initial step towards examining the activity, we constructed a high-copy number plasmid co-expressing hpaB and hpaC (pZE-HpaBC) and introduced it into *E. coli*. The resulting strain was cultivated and induced with IPTG for enzyme expression for 3 hours, after which 200 mg/L of substrate was added into the cultures. After additional 10 hour incubation, we analyzed the cell-free broth by HPLC. As shown in FIGS. 2A and 2B, the substrates umbelliferone and resveratrol were completely consumed and meanwhile two noticeable new peaks appeared (peaks 1 and 2). We further used naringenin to explore the substrate tolerance limit of HpaBC. With the same feeding experiment, we observed the majority of naringenin was left unconverted (FIG. 2C) and a small new peak was shown (peak 3). Since the activity towards naringenin was already low, we did not further test other molecules with larger size. The three new peaks were collected from HPLC for mass spectrum analysis. The positive mode of ESI-MS showed the ion peaks at m/z 179.0, 245.1 and 289.0 (M+H)+, equivalent to molecular weight of 178.0, 244.1 and 288.0, respectively (FIG. 2). The increase of 16 in the molecular weights correspond well with the hydroxylated products of the substrates umbelliferone (MW=162), resveratrol (MW=228) and naringenin (MW=272).

Figure 3:
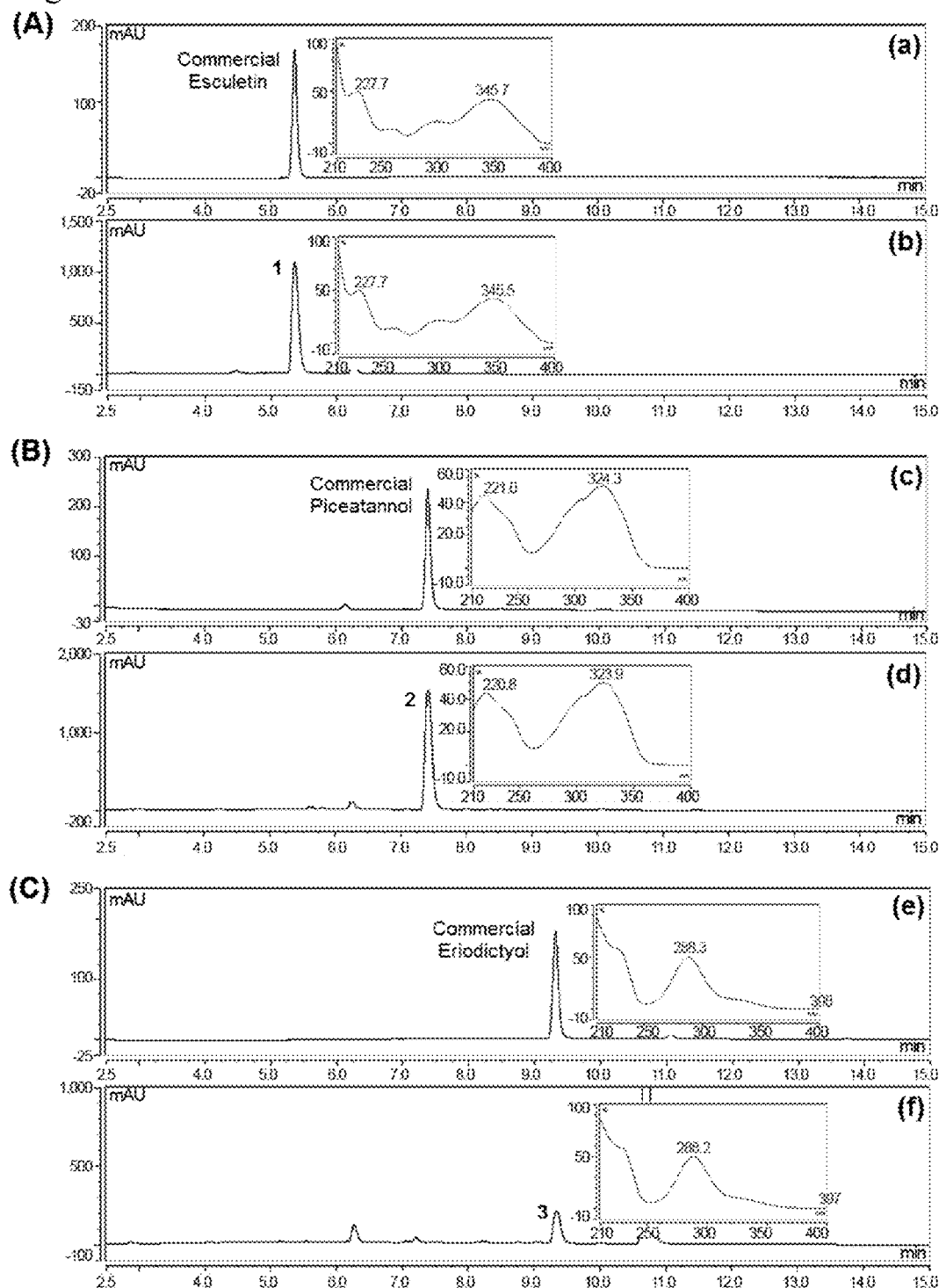
FIG. 3. Comparison of the retention times and UV adsorption profiles of the produced compounds with those of the corresponding commercial standards.

To further confirm the substitution positions of the hydroxyl group, larger amounts of the produced compounds were prepared for NMR analysis. 1H and 13C NMR spectra confirmed that the compounds of peaks 1 and 2 are the orthohydroxylated products esculetin and piceatannol, respectively; meanwhile 1H spectrum of peak 3 was also consistent with the reported NMR data of eriodictyol. Moreover, the retention times and UV absorption spectra of the 3 peaks are exactly identical to those of the corresponding commercial standards (FIG. 3). Therefore we concluded that the generated compounds were esculetin (Peak 1), piceatannol (Peak 2) and eridoctyol (Peak 3). These experimental evidences confirmed that HpaBC is able to perform orthohydroxylation of plant phenylpropanoids umbelliferone, resveratrol, and naringenin (FIG. 4).

Figure 5:
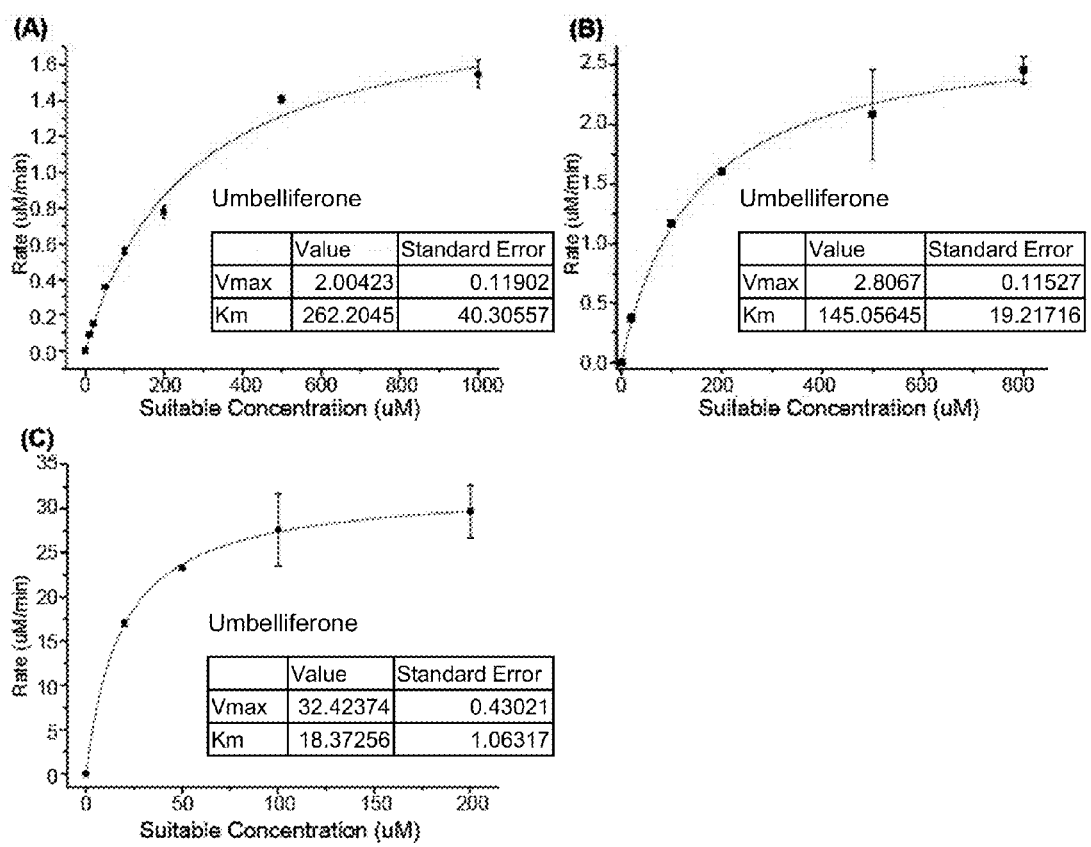
FIG. 5. Kinetic parameters of HpaBC towards umbelliferone (A), resveratrol (B) and 4HPA (C). The Km and Vmax values were determined using OriginPro8™ through non-linear regression of the Michaelis-Menten equation. kcat values were calculated according to the formula kcat=Vmax/[E]. Each data point is an average value of two independent experiments.

We further investigated and compared the kinetic parameters of HpaBC towards its native substrate 4HPA and the 3 non-native substrates. To do these, a multi-histidine tag was fused to the N-terminus of HpaB and HpaC, which were subsequently over-expressed and purified from *E. coli*. The enzyme complex was reconstituted in vitro for enzyme assays (FIG. 5). As shown in Table 1, the calculated apparent kinetic parameters indicated that the enzyme has relatively lower affinity and activity towards umbelliferone (Km=262.2 μM; kcat=4.0 min-1) and resveratrol (Km=145.1 μM; kcat=5.6 min-1) than towards 4HPA (Km=18.4 μM; kcat=64.8 min-1). The kinetic parameters towards naringenin were not determined due to the low activity.

TABLE 1

Kinetic parameters of HpaBC towards substrates

| Substrate | Km (μM) | kcat (min$^{-1}$) | kcat/Km (S$^{-1}$ · M$^{-1}$) |
|---|---|---|---|
| Umbelliferone | 262.2 ± 40.3 | 4.0 ± 0.1 | 254.3 |
| Resveratrol | 145.1 ± 19.3 | 5.6 ± 0.2 | 643.2 |
| 4-HPA | 18.4 ± 1.1 | 64.8 ± 0.9 | 58695.7 |

Whole-cell biocatalysis is an efficient and economical way to scale up enzyme-catalyzed reactions. On one hand, the wellestablished microbial expression systems such as *E. coli* and *Saccharomyces cerevisiae* are easy and inexpensive to grow and to produce enzymes; on the other hand, intact host cells can also supply required cofactors, such as FAD$^+$/FADH$_2$ and NAD(P)$^+$/NAD(P)H. To explore the potential of using HpaBC in whole-cell biocatalysis, we designed and conducted whole cell bioconversion experiments by resuspending *E. coli* cells over-expressing HpaBC in modified M9 medium at about 3.3 g/L DCW (OD$_{600}$=9.6±0.1) with the addition of 500 mg/L of umbelliferone or resveratrol. We observed that the substrates were completely converted into the corresponding hydroxylated products in 3 h, indicating high hydroxylation activity and regio-selectivity.

Figure 6:
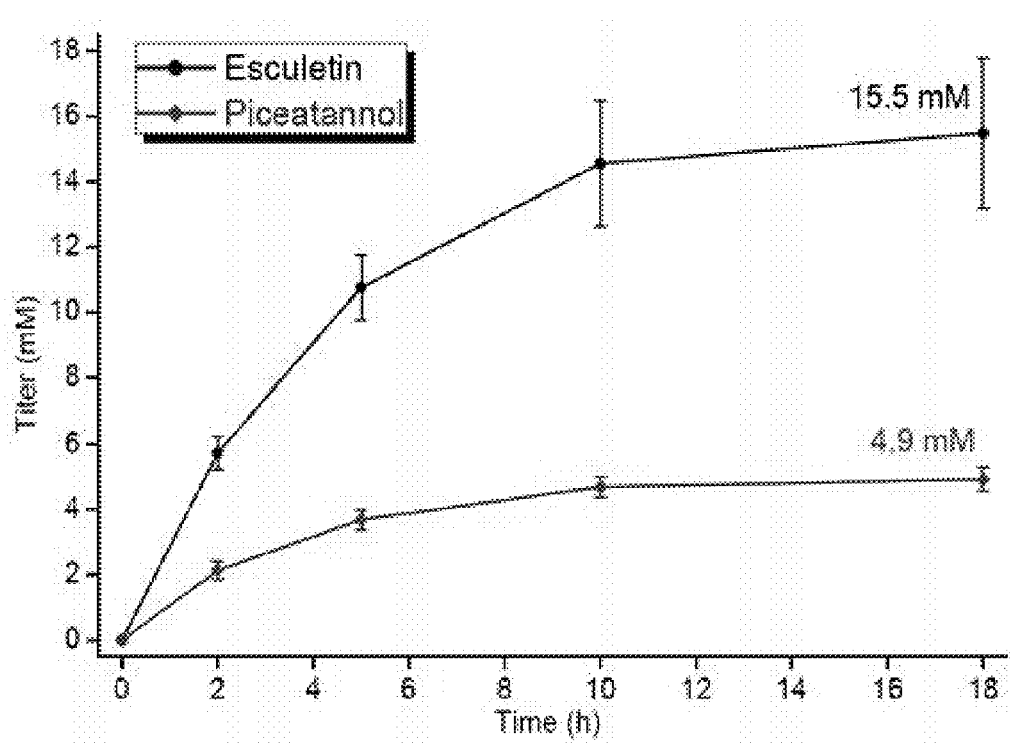
FIG. 6. Production of esculetin and piceatannol by whole-cell catalysis from umbelliferone and resveratrol.

To explore the maximum whole-cell biocatalytic capacity, we used a higher initial concentration of the substrates (1.5 g/L) and kept feeding the cells when the substrates' concentration fell below 0.5 g/L. As shown in FIG. 6, the hydroxylation reactions exhibited the highest rates in the initial 2 h, which were 298.1 and 110.9 μM/h/OD for esculetin and piceatannol, respectively. Then the conversion rates gradually decreased for both substrates. By the end of 18 h, the titers of the products reached the maximums (2.7 g/L or 15.5 mM for esculetin; and 1.2 g/L or 4.9 mM for piceatannol). Although the supplemented substrates were not completely converted, the molar yields (product formed/substrate consumed) for both reactions were over 98%. In addition, when 150 mg/L of naringenin was fed, 16.7 mg/L (58 µM) of eriodictyol was generated in 10 h with the majority of the substrate left unconverted. It should be noted that the supplementation of 1.5 mM of ascorbic acid (vitamin C) was necessary to maintain the high yields, since the products and substrates, especially piceatannol, are easily to get oxidized under aerobic conditions. Without ascorbic acid supplementation, the titer of piceatannol decreased by 25% with the consumption of even larger amount of resveratrol, suggesting that resveratrol and piceatannol could be spontaneously oxidized. Moreover, we observed that the whole-cell conversion efficiency towards umbelliferone is about 3-fold higher than that towards resveratrol, which is not exactly consistent with their relative activities in vitro (Table 1). One possible explanation is that that umbelliferone might have higher diffusion rate through the cell membrane owing to its smaller size and more compact molecule structure. Piceatannol production rate might be limited by its diffusion rate.

In this study, we established an efficient biocatalytic platform to regioselectively hydroxylate complex phenolic compounds. To our knowledge, this is the first report of esculetin production via umbelliferone hydroxylation. This work also reported the highest level of piceatannol production achieved so far via biotechnological approaches.

According to our results and previous reports, HpaBC is a promiscuous monooxygenase that can catalyze orthohydroxylation of a series of phenolic compounds, from the simplest molecule phenol to the complex phenylpopanoids (FIG. 1). These molecules share the p-hydroxyl-benzyl ring moiety which is a featured structure recognized by HpaB. As long as the other parts of the substrates can fit in the catalytic pocket, hydroxylation can happen. However, it also should be noted that hydroxylation of the substrates with larger size (e.g. piceatannol and esculetin) is not as efficient as that of the native substrate 4HPA, and naringenin is an even poorer substrate due to its oversized molecule structure.

Despite of its high catalytic efficiency and versatility, the structure information of the *E. coli* HpaB is still not available. Although the crystal structure of its counterpart from *Thermus thermophilus* has been resolved (Kim et al., *J. Biol. Chem.*, 2007, 282, 33107-331), the low sequence identity does not guarantee reliable homology modeling. It will be helpful to resolve the crystal structure of the *E. coli* HpaB, based on which further study of the structure-function relationship of this important non-P450 can be performed. Overall, this enzyme (HpaBC) holds great potential to form a novel biocatalytic hydroxylation platform technology.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for producing an ortho-hydroxylated phenylpropanoid comprising:

culturing a microbe comprising HpaBC activity in the presence of a phenylpropanoid substrate under conditions suitable to ortho-hydroxylate the phenylpropanoid substrate to result in an ortho-hydroxylated phenylpropanoid, wherein the microbe comprises coding regions encoding HpaB and HpaC, the HpaB comprising an amino acid sequence having at least 95% sequence identity with the amino acid sequence of SEQ ID NO:1, and the HpaC comprising an amino acid sequence having at least 95% sequence identity with the amino acid sequence of SEQ ID NO:2, wherein the phenylpropanoid substrate comprises a first six-carbon ring and at least one additional cyclic structure, and wherein the phenylpropanoid substrate comprises a structure having the formula

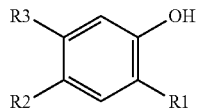

wherein R1 is the position at which the phenylpropanoid substrate is ortho-hydroxylated by HpaBC, and wherein R2 is a divalent organic linking group that comprises the additional cyclic structure and wherein R3 is a hydrogen or a nonring substituent, or wherein R2 is joined to R3 to form the additional cyclic structure; and isolating the ortho-hydroxylated phenylpropanoid from the microbe or the culture medium, or the combination thereof.

2. The method of claim 1 wherein the divalent organic linking group is a linear hydrocarbon group.

3. The method of claim 2 wherein the linear hydrocarbon group comprises between 0 and 20 carbons.

4. The method of claim 2 wherein the linear hydrocarbon group comprises at least one unsaturated bond.

5. The method of claim 1 wherein the additional cyclic structure is a 5 atom ring.

6. The method of claim 1 wherein the additional cyclic structure is a 6 atom ring.

7. The method of claim 6 wherein the ring is a heterocycle.

8. The method of claim 1 wherein the R3 is selected from a halogen, a nitrile, a hydroxy, an alkoxy (OR), a nitrate, a nitrite, a sulfate (O—SO$_3$R), an amino (NR$_2$), a nitro, a sulfonate (SO$_2$OR), or a C1-C10 organic group, with each R independently being hydrogen or an organic group.

9. The method of claim 1 wherein one or more hydrogen-bearing carbon atoms in the first six-carbon ring is substituted, wherein each substituent is selected from a halogen, a nitrile, a hydroxy, an alkoxy (OR), a nitrate, a nitrite, a sulfate (O—SO$_3$R), an amino (NR$_2$), a nitro, a sulfonate (SO$_2$OR), or a C1-C10 organic group, wherein each R is independently a hydrogen or an organic group.

10. The method of claim 1 wherein one or more hydrogen-bearing carbon atoms in the additional cyclic structure is substituted, wherein each substituent is selected from a halogen, a nitrile, a hydroxy, an alkoxy (OR), a nitrate, a nitrite, a sulfate (O—SO$_3$R), an amino (NR$_2$), a nitro, a sulfonate (SO$_2$OR), or a C1-C10 organic group, wherein each R is independently a hydrogen or an organic group.

11. The method of claim 1 wherein the phenylpropanoid substrate comprises a coumarin structure.

12. The method of claim 11 wherein the phenylpropanoid substrate comprising the coumarin structure is umbelliferone.

13. The method of claim 1 wherein the phenylpropanoid substrate comprises a stilbene structure.

14. The method of claim 13 wherein the phenylpropanoid substrate comprising the stilbene structure is reserveratrol.

15. The method of claim 1 wherein the phenylpropanoid substrate comprises a flavonoid structure.

16. The method of claim 15 wherein the flavonoid structure is a flavone.

17. The method of claim 1 wherein the microbe is *E. coli*.

18. The method of claim 1 wherein the HpaBC activity is endogenous to the microbial cell.

19. The method of claim 1 wherein the microbe is a genetically engineered cell comprising greater HpaBC activity than a control microbe.

20. The method of claim 1 wherein the culturing further comprises adding the phenylpropanoid substrate.

21. The method of claim 1 wherein the phenylpropanoid substrate is produced by the microbe.

* * * * *

SEQUENCE LISTING

```
<160> NUMBER OF SEQ ID NOS: 6

<210> SEQ ID NO 1
<211> LENGTH: 520
<212> TYPE: PRT
<213> ORGANISM: Escherichia coli

<400> SEQUENCE: 1

Met Lys Pro Glu Asp Phe Arg Ala Ser Thr Gln Arg Pro Phe Thr Gly
1               5                   10                  15

Glu Glu Tyr Leu Lys Ser Leu Gln Asp Gly Arg Glu Ile Tyr Ile Tyr
            20                  25                  30

Gly Glu Arg Val Lys Asp Val Thr Thr His Pro Ala Phe Arg Asn Ala
        35                  40                  45
```

```
Ala Ala Ser Val Ala Gln Leu Tyr Asp Ala Leu His Lys Pro Glu Met
 50                  55                  60

Gln Asp Ser Leu Cys Trp Asn Thr Asp Thr Gly Ser Gly Gly Tyr Thr
 65                  70                  75                  80

His Lys Phe Phe Arg Val Ala Lys Ser Ala Asp Asp Leu Arg His Glu
                 85                  90                  95

Arg Asp Ala Ile Ala Glu Trp Ser Arg Leu Ser Tyr Gly Trp Met Gly
                100                 105                 110

Arg Thr Pro Asp Tyr Lys Ala Phe Gly Cys Ala Leu Gly Gly Thr
                115                 120                 125

Pro Gly Phe Tyr Gly Gln Phe Glu Gln Asn Ala Arg Asn Trp Tyr Thr
                130                 135                 140

Arg Ile Gln Glu Thr Gly Leu Tyr Phe Asn His Ala Ile Val Asn Pro
145                 150                 155                 160

Pro Ile Asp Arg His Leu Pro Thr Asp Lys Val Lys Asp Val Tyr Ile
                165                 170                 175

Lys Leu Glu Lys Glu Thr Asp Ala Gly Ile Ile Val Ser Gly Ala Lys
                180                 185                 190

Val Val Ala Thr Asn Ser Ala Leu Thr His Tyr Asn Met Ile Gly Phe
                195                 200                 205

Gly Ser Ala Gln Val Met Gly Glu Asn Pro Asp Phe Ala Leu Met Phe
                210                 215                 220

Val Ala Pro Met Asp Ala Asp Gly Val Lys Leu Ile Ser Arg Ala Ser
225                 230                 235                 240

Tyr Glu Met Val Ala Gly Ala Thr Gly Ser Pro Tyr Asp Tyr Pro Leu
                245                 250                 255

Ser Ser Arg Phe Asp Glu Asn Asp Ala Ile Leu Val Met Asp Asn Val
                260                 265                 270

Leu Ile Pro Trp Glu Asn Val Leu Leu Tyr Arg Asp Phe Asp Arg Cys
                275                 280                 285

Arg Arg Trp Thr Met Glu Gly Gly Phe Ala Arg Met Tyr Pro Leu Gln
                290                 295                 300

Ala Cys Val Arg Leu Ala Val Lys Leu Asp Phe Ile Thr Ala Leu Leu
305                 310                 315                 320

Lys Lys Ser Leu Glu Cys Thr Gly Thr Leu Glu Phe Arg Gly Val Gln
                325                 330                 335

Ala Asp Leu Gly Glu Val Val Ala Trp Arg Asn Thr Phe Trp Ala Leu
                340                 345                 350

Ser Asp Ser Met Cys Ser Glu Ala Thr Pro Trp Val Asn Gly Ala Tyr
                355                 360                 365

Leu Pro Asp His Ala Ala Leu Gln Thr Tyr Arg Val Leu Ala Pro Met
                370                 375                 380

Ala Tyr Ala Lys Ile Lys Asn Ile Ile Glu Arg Asn Val Thr Ser Gly
385                 390                 395                 400

Leu Ile Tyr Leu Pro Ser Ser Ala Arg Asp Leu Asn Asn Pro Gln Ile
                405                 410                 415

Asp Gln Tyr Leu Ala Lys Tyr Val Arg Gly Ser Asn Gly Met Asp His
                420                 425                 430

Val Gln Arg Ile Lys Ile Leu Lys Leu Met Trp Asp Ala Ile Gly Ser
                435                 440                 445

Glu Phe Gly Gly Arg His Glu Leu Tyr Glu Ile Asn Tyr Ser Gly Ser
                450                 455                 460
```

Gln Asp Glu Ile Arg Leu Gln Cys Leu Arg Gln Ala Gln Ser Ser Gly
465                 470                 475                 480

Asn Met Asp Lys Met Met Ala Met Val Asp Arg Cys Leu Ser Glu Tyr
            485                 490                 495

Asp Gln Asn Gly Trp Thr Val Pro His Leu His Asn Asn Asp Asp Ile
        500                 505                 510

Asn Met Leu Asp Lys Leu Leu Lys
        515                 520

<210> SEQ ID NO 2
<211> LENGTH: 170
<212> TYPE: PRT
<213> ORGANISM: Escherichia coli

<400> SEQUENCE: 2

Met Gln Leu Asp Glu Gln Arg Leu Arg Phe Arg Asp Ala Met Ala Ser
1               5                   10                  15

Leu Ser Ala Ala Val Asn Ile Ile Thr Thr Glu Gly Asp Ala Gly Gln
            20                  25                  30

Cys Gly Ile Thr Ala Thr Ala Val Cys Ser Val Thr Asp Thr Pro Pro
        35                  40                  45

Ser Leu Met Val Cys Ile Asn Ala Asn Ser Ala Met Asn Pro Val Phe
50                  55                  60

Gln Gly Asn Gly Lys Leu Cys Val Asn Val Leu Asn His Glu Gln Glu
65                  70                  75                  80

Leu Met Ala Arg His Phe Ala Gly Met Thr Gly Met Ala Met Glu Glu
            85                  90                  95

Arg Phe Ser Leu Ser Cys Trp Gln Lys Gly Pro Leu Ala Gln Pro Val
            100                 105                 110

Leu Lys Gly Ser Leu Ala Ser Leu Glu Gly Glu Ile Arg Asp Val Gln
        115                 120                 125

Ala Ile Gly Thr His Leu Val Tyr Leu Val Glu Ile Lys Asn Ile Ile
        130                 135                 140

Leu Ser Ala Glu Gly His Gly Leu Ile Tyr Phe Lys Arg Arg Phe His
145                 150                 155                 160

Pro Val Met Leu Glu Met Glu Ala Ala Ile
            165                 170

<210> SEQ ID NO 3
<211> LENGTH: 56
<212> TYPE: DNA
<213> ORGANISM: artificial
<220> FEATURE:
<223> OTHER INFORMATION: synthetic oligonucleotide primer

<400> SEQUENCE: 3
gggaaaggta ccatgcatca ccatcatcac caccataaac cagaagattt ccgcgc         56

<210> SEQ ID NO 4
<211> LENGTH: 40
<212> TYPE: DNA
<213> ORGANISM: artificial
<220> FEATURE:
<223> OTHER INFORMATION: synthetic oligonucleotide primer

<400> SEQUENCE: 4
gggaaagcat gcttatttca gcagcttatc cagcatgttg                           40

```
<210> SEQ ID NO 5
<211> LENGTH: 58
<212> TYPE: DNA
<213> ORGANISM: artificial
<220> FEATURE:
<223> OTHER INFORMATION: synthetic oligonucleotide primer

<400> SEQUENCE: 5
gggaaaggta ccatgcatca ccatcatcac caccatcaat tagatgaaca acgcctgc          58

<210> SEQ ID NO 6
<211> LENGTH: 37
<212> TYPE: DNA
<213> ORGANISM: artificial
<220> FEATURE:
<223> OTHER INFORMATION: synthetic oligonucleotide primer

<400> SEQUENCE: 6
gggaaagcat gcttaaatcg cagcttccat ttccagc                                 37
```